(12) United States Patent
Amasino et al.

(10) Patent No.: US 7,420,102 B2
(45) Date of Patent: Sep. 2, 2008

(54) DWARFISM GENES AND DWARF PLANTS

(75) Inventors: Richard M Amasino, Madison, WI (US); Fritz M Schomburg, Madison, WI (US); Scott D Michaels, Madison, WI (US); Colleen M. Bizzell, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 358 days.

(21) Appl. No.: 11/152,892

(22) Filed: Jun. 15, 2005

(65) Prior Publication Data

US 2005/0251883 A1 Nov. 10, 2005

Related U.S. Application Data

(62) Division of application No. 10/155,435, filed on May 23, 2002, now Pat. No. 6,921,849.

(51) Int. Cl.
*C12N 15/29* (2006.01)
*C12N 15/82* (2006.01)
*A01H 5/00* (2006.01)

(52) U.S. Cl. .................... 800/298; 536/23.6; 435/320.1

(58) Field of Classification Search ........................ None
See application file for complete search history.

(56) References Cited

U.S. PATENT DOCUMENTS 5,939,539 A  8/1999  Lange et al.
6,198,021 B1  3/2001  Lange et al.

OTHER PUBLICATIONS

Biemelt et al (2004, Plant Physiology 135:254-265).*
Bowie et al, Science 247:1306-1310, 1990.*
McConnell et al, Nature 411 (6838):709-713, 2001.*
Carrera, E., et al., "Changes in GA 20-oxidase gene expression strongly affect stem length . . ." Plant J., 22(3), 247-256, 2000.
Chasan, R., et al., "GA Biosynthesis: a glimpse at the genes." Plant Cell, 7, 141-143, 1995.
Coles, J.P., et al., "Modification of gibberellin production and plant development in Arabidopsis by sense and antisense . . ." Plant J., 17(5), 547-556, 1999.
Curtis, I.S., et al., "Induction of dwarfism in transgeneic *Solanum dulcamara* by over-expression of a gibberellin 20-oxidase . . ." Plant J., 23(3), 329-338, 2000.
Harberd, N.P., et al., "Gibbeerellin: inhibitor of an inhibitor of . . ." BioEssays, 20, 1001-1008, 1998.
Hedden, P., et al., "Genetic analysis of gibberellin biosynthesis." Plant Physiol., 119, 365-370, 1999.
Hedden, P., et al., "Gibberellin metabolism: new insights revealed by the genes." Trends Plant Sci, 5(12), 523-530, 2000.

Hedden, P., et al., "Gibberellin biosynthesis: enzymes, genes, and their regulation." Annu. Rev. Plant Physiol. Plant Mol. Biol., 48, 431-60, 1997.
Hedden, P., et al., "Manipulation of hormone biosynthetic genes in transgenic plants." Curr. Opin. in Biotech., 11, 130-137, 2000.
Hedden, P., "Recent advances in gibberellin biosynthesis." J. Expt. Bot., 50(334), 553-563, 1999.
Huang, S., et al., "Overexpression of 20-oxidase confers a gibberellin-overproduction phenotype in Arabidopsis." Plant Physiol., 118, 773-781, 1998.
Jones, R., et al., "Gibberellins 2000." Trends Plant Sci., 5(8), 320-321, 2000.
Martin, D.N., et al., "The Slender gene of pea encodes a gibberellin 2-oxidase." Plant Physiol., 121, 775-781, 1999.
Peng, J., et al., "'Green revolution' genes encode mutant gibberellin response modulators." Nature, 400, 256-26, 1999.
Phillips, A.L., "Gibberellins in Arabidopsis." Plant Physiol. Biochem., 36(1-2), 115-124, 1998.
Phillips, A.L., et al., "Isolation and expression of three gibberellin 20-oxidase cDNA clones from Arabidopsis." Plant Physiol., 108, 1049-1057, 1995.
Prescott, A.G., et al., "Dioxygenases: molecular structure and role in plant metabolism." Annu. Rev. Plant Physiol. Plant Mol. Biol., 47, 245-71, 1996.
Ross, J.J., et al., "Gibberellin mutants." Physiol. Plantarum, 100, 550-560, 1997.
Ross, J.J., "Recent Advances in the study of gibberellin mutants." Plant Growth Regulation, 15, 193-206, 1994.
Sakamoto, T., et al., "Expression of a gibberellin 2-oxidase gene around the shoot apex is related to phase transition in rice." Plant Physiol., 125, 1508-1516, 2001.
Silverstone, A.L., et al., "Gibberellins and the green revolution." Trends Plant Sci., 5(1), 1-2, 2000.
Thomas, S.G., et al., "Molecular cloning and functional expression of gibberellin 2-oxidases, multifunctional enzymes involved in gibberellin deactivation." Proc. Natl. Acad. Sci. USA, 96, 4698-4703, 1999.
Weigel, D., et al., "Activation tagging in Arabidopsis." Plant Physiol., 122, 1003-1013, 2000.
Yamaguchi, S., et al., "Gibberellin biosynthesis: its regulation by endogenous and environmental signals." Plant Cell Physiol., 41(3), 251-257, 2000.
GenBank Accession No. AC079284.
Lin et al, (Jan. 2001, NCBI Accession No. AC079284).

* cited by examiner

*Primary Examiner*—Stuart F. Baum
(74) *Attorney, Agent, or Firm*—Quarles & Brady LLP

(57) ABSTRACT

The present invention discloses the function, the cDNA sequences, and the expressed amino acid sequences of two genes the expression of which reduced bioactive GA levels and the height of a plant. This information enables creation of dwarf transgenic plants or transgenic plants with a specific dwarf organ.

6 Claims, 2 Drawing Sheets

Fig. 1

```
SEQ ID NO:4   L10   1   MASQPPFKTNFCSIFGSSFPNSTSDSN....TNTSTIQTSGLKLPVIDLS  46
                        |||   : .:   .   | .| .    ..|    ..|||||.|
SEQ ID NO:6   69    1   ..MDPPFNEIYNNLLYNQITNKENDVSEIPFSFSVTAVVEEVELPVIDVS 48

L10   47  HLTSGEEVKRKRCVKQMVAAAKEWGFFQIVNHGIPKDVFEMMLLEEKKLF  96
                        |  | |  .|.:|  ..  |.:|||||||::||||  || | |  |: :.|
              69    49  RLIDGAEEEREKCKEAIARASREWGFFQVINHGISMDVLEKMRQEQIRVF 98

L10   97  DQPFSVKVR.ERFSDLSKNSYRWGNPSATSPAQYSVSEAFHIILSEVSRI  145
                        :||   | : |:|    |   |||||  |||||  | | |||||: :.::|
              69    99  REPFDKKSKSEKF...SAGSYRWGTPSATSIRQLSWSEAFHVPMTDISD.  144

L10   146 SDDRNNLRTIVEAYVQEIARVAQMICEILGKQVNVSSEYFENIFELENSF  195
                        . |    | ..|: |  .| |:  |:|  ..     | :|.           :
              69    145 NKDFTTLSSTMEKFASESEALAYMLAEVLAEKAGQKSSFFKENCVRNTCY  194

L10   196 LRLNKYHPSVFGSEVFGLVPHTDTSFLTILSQDQIGGLELENNGQWISVK  245
                        ||:|:| |    |||:||.||||.  |||||  |||:|||:|   . .||.||
              69    195 LRMNRYPPCPKPSEVYGLMPHTDSDFLTILYQDQVGGLQLIKDNRWIAVK  244

L10   246 PCLEALTVNIGDMFQALSNGVYQSVRHRVISPANIERMSIAFFVCPYLET  295
                        |  .||  :|||||:|||  |||.|.||  |||..     :||  |  |:|.||    :
              69    245 PNPKALIINIGDLFQAWSNGMYKSVEHRVMTNPKVERFSTAYFMCPSYDA  294

L10   296 EIDCFGYPKKYRRFSFREYKEQSEHDVKETGDKVGLSRFLI...  336
                        |:|    ||  ||||||:::|  :   |||. | ||||  |||
              69    295 VIECSSDRPAYRNFSFREFRQQVQEDVKKFGFKVGLPRFLNHVY 338
```

Fig. 2

```
SEQ ID NO:7   Atga2ox1    1 ----------------------------------------MA LSKPVAIPKSGF
SEQ ID NO:8   atga2ox2    1 --------------------------------- VLPQPVTL HIS IP KPVP TS
SEQ ID NO:9   Atga2ox3    1 --------------------------------- IVLQPASF SNLY NPKCKPRP----
SEQ ID NO:10  GA20ox1     1 MAILCTTTSPAEKEHEPKQDLEKDQTSP IF PSLL QSQIP QFIW DEEKP ID PE
SEQ ID NO:11  GA5         1 MAVSFVTTSPEEEDKPKLG--IGNIQTP IF PSML QANIP QFIW DDEKP INV E
SEQ ID NO:6   69          1 ------------------ DPP NE YN LL YN ITNKEN VS IP S VT VVEE
SEQ ID NO:4   L10         1 ----------------MASQ PP KTN CS FGSSFP STS SNTN---- S IQTSG
SEQ ID NO:12  GA4         1 ------MPAMLTDVFRGHPIH PHSHIPD TS RELPD Y WTPKD L SA P PPATG Atga2ox1    16 SL PVID S---------DPES HP VK CED GF KVINHGV AE SV EH T DF S
              atga2ox2    29 HS PV N ---------DPEA TR VK ACEE GF KV NHGVRP L TR EQ A GF G
              Atga2ox3    25 L PVID L ---------DSDA TQ VK ACEE GF KVINHG RP D TQ E QE A NF A
              GA20ox1     61 N PF D S ----SQ STLEAPRV AE C TKH GF L V NHGV ES I ADA RLMESF D
              GA5         59 DV L D QN S-DPSSTLDASRL SE C KH GF KH V NHG ES I SDA E YTS F D
              69          40  E PVID SRL DGAE E E CK A IARAS EWGFF QV INHGISM DVLEKMRQE IRV R
              L10         38  K PVI SH TS E EVK K QV KQ VA AK EWGFF Q NHGI PK V FE MLL K E D
              GA4         55 EN L D D ---------  PDATNQ I C  TWGAF SNHGV P G L D EFLTGS G Atga2ox1    67 L KSE QVAG---YP GYGNS IC -RN DVGWVEYLLMNANHDSGSGG----PLFPSLL
              atga2ox2    80 L QSL N AGPP-- P YGY NK IC - N DVGWIEYLLLNANPQ SP-----KTSAVFR
              Atga2ox3    76 LHHSL D AGPP-- P GY K IC - N DLGWLEYILLNAN C ESH-----KTTAIFR
              GA20ox1    116 M LAG Q QRKPG SCGY SFTG RF TKLPWKE LS FQ SNDN GSRTVQDYFSDTLG
              GA5        118 M LSE Q VLRKSG SVGY SFTG RF TKLPWKE LS FR CDD SRSKSVQDYFCDALG
              69         100  P D KSKS----- K SA GSYR WGT SATS I R LSWSE AF HV M DIS DN---------
              L10         98  P SV V ERF---SDL SKNS YR WGN SA S PA YS V SEAF H I SE S RIS--------
              GA4        106 L VQ BL KS ARSETGVSGY V B I S FFNKQ WSEG ITGSPLNDFR-----KLWP---

Atga2ox1   119  SPG FRNA E T SVRK T D LE KI TE GLG I PRNTLSKL SDQN--TDSIL N Y
              atga2ox2   132 QTPQI FRNA E T SVRK T D LE KI TE GLG I PRNTLSKL SDQN--TDSIL N Y
              Atga2ox3   128  TPAI FREA E Y IKE MKR SKFL EE ELKIEPKEKSRL VKE--SDSC RMNH Y
              GA20ox1    176 Q EQFGKVY D CEAMS L LK ME L GLSL VNRD FGFFE---E--NDSI N Y
              GA5        178  G QPFGKVY E CEAMS L LK ME L GLSL V RD FFE---E--NDSI N YY
              69         146 KD T L S T K ASE SE ALAYM AB V AK AG KSS EKNCV ------NTC YLRMNRY
              L10        147 D RNN L R I AM VQ EIARV  M C E GKQVNVS S EN IFEL-----ENS L N Y
              GA4        158 QHHLNYCDI E EEHMKK L SKLMW ALNSL VSEEDIEWAS SSDLNWAQAAL Q N Y Atga2ox1   177 PPCP LSNKKTNGGKN I GFGE TD PQI S LRS T SGL Q NL DGS S VP HTS FFF
              atga2ox2   190 PPCP LSNKKTNGGKN I GFGE TD PQI S LRS T SGL Q NL DGS S VP HTS FFF
              Atga2ox3   186  ---E--KEETPVKE EI GFGE TD PQL S LRS DTEGL Q CVK GT D T P HS EFF
              GA20ox1    231 PPCQT P -------DLTL GTGP CD PSS TI H D VNGL FVDN- Q S PNPK FV
              GA5        233 PPCI K P -------DLTL GTGP C PTS TI H D VNGL FVEN- Q RS PNPK FV
              69         201 PPCPK F -------SEVYGL M PHTDS DFLT ILYQDQVGGL Q IKDN- RWIAVKPNPKALI T
              L10        202 H SVFG-------SEV GL PHTDS FLTI SQD I GGL ENN G- QW SVKPCLEALT
              GA4        218  VC EF -------DRAMG AA HTDSTLLTILYC NT GLQVF DDLG T V PPF GSL W Atga2ox1   237 N GDSL QVM NG REKSVRHRV A N CKS VSMI Y AG P SLTQR APL CLIDNE DERL E
              atga2ox2   250 N GDSL QVM NG REKSVRHRV A N CKS VSMI Y AG P SLTQR APL CLIDNE DERL E
              Atga2ox3   241 L GDTL QVM NG RE KSVKHRV T RS I SMI Y AG P LSEK APL SCLVPKQ DCL N
              GA20ox1    283 NIGDT M LSNG EKSCL A VNRESA KSM E C KK V KPP SDILEKMKTRK YP
              GA5        285 NIGDT M LSN DR KSCL A VNSKS PKSLA F CPKK RV TPPRELLDSITSRR YP
              69         253 NIGDLF Q WSNGMYKSVE RVM N PKVEF STAYF MCPSY AV IECS S ------ DRE A
              L10        254 NIGD F Q LSNG VY QSVR RV S PAN ERMSI E FC YLTEI DCFG------YPKK R
              GA4        271 N GDL H IL SHG FKSVL ARV NQTRA L SVA L LWG QSD IK SPVPKLVSPV E PL Q Atga2ox1   297 E T SE NSTYNSRLSDN- QQFERKTIKNLLN-
              atga2ox2   310 E T SE NSTYNSRLSDN- QQFERKTIKNLLN-
              Atga2ox3   301 E SQ L LSAYKTKLGDY- L GI FEKRPPFSLSNV
              GA20ox1    343 F SM LF TCKHY ADVNT DSFSNWVITNNNPI
              GA5        345 D TA SM LF TCKHY ADMNT QAFSDWLTKPI---
              69         307 NFS RE RQ V QEDVK F GF KVGI PRF NHVY----
              L10        308 R S REY Q SEHD SETC KVG SR I-------
              GA4        331 SV WK E LRTKATHFN ALSM RNH EE---------
```

DWARFISM GENES AND DWARF PLANTS

CROSS-REFERENCE TO RELATED APPLICATIONS

This application is a divisional application of U.S. patent application Ser. No. 10/155,435, filed on May 23, 2002, now U.S. Pat. No. 6,921,849 which is herein incorporated by reference.

STATEMENT REGARDING FEDERALLY SPONSORED RESEARCH OR DEVELOPMENT

This invention was made with United States government support awarded by the following agency: DOE DE-FCO5-92QR22072. The United States has certain rights in this invention.

BACKGROUND OF THE INVENTION

Gibberellins (GAs) are a group of tetracyclic diterpene carboxylic acids involved in a variety of developmental processes. They were originally identified through their effect on stem elongation (Phillips, A. L., Plant Physiol. Biochem 36: 115-124, 1998), and are now implicated in all stages of the plant life cycle including seed germination, leaf expansion, floral induction, fruit maturation, and apical dominance (Harberd, N. P. et al., BioEssays 20: 1001-1008, 1998). There are at least 126 different GAs identified in plants, fungi, and bacteria; however, most are precursors or degradation products, which are inactive forms. The bioactive GAs in higher plants include GA1, GA3, GA4, and GA7 (Hedden, P. and A. L. Phillips, Trends Plant Sci. 5: 523-530, 2000).

The GA biosynthetic pathway has three different classes of enzymes that catalyze specific reactions in the synthesis of bioactive GAs: terpene cyclases, Cyt P450 monooxygenases, and 2-oxoglutarate-dependent dioxygenases (Yamaguchi, S. and Y. Kamiya, Plant Cell Physiol. 41: 251-257, 2000). The first set of reactions of the biosynthetic pathway, from trans-geranylgeranyl diphosphate (GGPP) to GA12-aldehyde, is the same in all systems that have been studied. GGPP is converted to ent-kaurene via the terpene cyclases. ent-kaurene is then oxidized by Cyt P450 monooxygenases to GA12-aldehyde, GA12 and then GA53. GA12 and GA53 are the initial substrates for the 2-oxoglutarate-dependent dioxygenases. The specific enzymatic steps for the synthesis of bioactive GAs from GA12 are species specific.

The last reactions producing bioactive GAs and the first breakdown reactions involve several types of dioxygenases. The nomenclature of these dioxygenases is variable throughout the literature. Herein, the most commonly used name is listed first, followed by any other names also used. GA 20-oxidases remove the C-20, whereas 3β-hydroxylases (also called 3-oxidases) introduce the 3β-hydroxyl group; both are steps on the way to bioactive GAs. GA 2-oxidases (also called 2β-hydroxylases) introduce a 2β-hydroxyl group resulting in inactive products that cannot be converted to active forms (Thomas, S. G. et al., Proc. Natl. Acad. Sci. USA 96: 4698-4703, 1999). GA 2-oxidases generally act on GAs with 19 carbons, although there is evidence of 2β-hydroxylation of C20-GAs (Hedden, P. and Y. Kamiya, Annu. Rev. Plant Physiol. Mol. Biol. 48: 431-60, 1997).

GA-modifying enzymes produce a vast number of GAs, although most are precursors or inactive forms. Many dioxygenases have been shown to be multifunctional, catalyzing consecutive reactions in the pathway, or modifying different, but structurally similar, GAs. For example, GA5, a GA 20-oxidase, converts GA12 to GA15 to GA24 to GA9, and GA53 to GA20 (Yamaguchi, S. and Y. Kamiya, Plant Cell Physiol. 41: 251-257, 2000). This multifunctional property allows many different GAs to be formed from relatively few enzymes.

Several of the dioxygenases can be grouped into small gene families. In *Arabidopsis*, GA 20-oxidases and GA 3β-hydroxylases are each encoded by at least four genes, and GA 2-oxidases are claimed in one review to be encoded by at least six genes (Hedden, P. and A. L. Phillips, Trends Plant Sci. 5: 523-530, 2000). Although the three groups of dioxygenases act on similar GA substrates, cluster analysis shows that they are no more closely related to each other than to any other plant dioxygenase (Hedden, P. and A. L. Phillips, Trends Plant Sci. 5: 523-530, 2000). The identity between different groups of GA dioxygenases is approximately 20-30% within one species, such as *Arabidopsis* (Table 1). Within a group, however, the identity is higher, even among species. *Arabidopsis* GA 20-oxidases are approximately 55-70% identical to each other, and 50-60% identical to 20-oxidases of other species (Prescott, A. G. and P. John, Annu. Rev. Plant Physiol. Plant Mol. Biol. 47: 245-71, 1996). The three published *Arabidopsis* GA 2-oxidases are 49-68% identical to each other (Thomas, S. G. et al., Proc. Natl. Acad. Sci. USA 96: 4698-4703, 1999), and 35-65% identical to GA 2-oxidases of other species (Table 2). The various members of each dioxygenase family are differentially expressed within the plant, and may be involved in different developmental processes (Hedden, P. and A. L. Phillips, Trends Plant Sci. 5: 523-530, 2000).

Chemical modification of GA levels is common in agriculture and horticulture. Seedless grapes are often treated with GA3 to increase berry size. Conversely, many crops and ornamental plants are treated with chemicals that act to inhibit enzymes in the GA-biosynthetic pathway (Hedden, P. and A. L. Phillips, Trends Plant Sci. 5: 523-530, 2000). Height reduction in ornamentals is currently achieved in many plants, such as poinsettias and petunias, via treatment with GA-inhibiting chemicals to produce compact plants that are more desired by consumers. Height reduction in a number of crop plants has resulted in increased yields and yield stability. In fact, compact crop plants have been a cornerstone of the great enhancements in agriculture yields over the past three decades. Compact plants can be grown more densely and are more resistant to storm damage (lodging) than taller wild type versions. Compact plants are easier to harvest because they hold the seed products closer together, reducing loss during harvesting.

Many groups have manipulated GA levels by transgenetically altering the expression of genes involved in GA metabolism. Overexpression of GA 20-oxidases in *Arabidopsis* has yielded plants with elevated GA levels which results in plants that are taller and have lighter green leaves than wild-type plants (Huang, S. et al., Plant Physiol. 118: 773-781, 1998). Suppression of GA 20-oxidases by antisense RNA has produced *Arabidopsis* plants that display phenotypes similar to weak GA-deficient plants; these plants have darker green cotyledons, were about 40% shorter than wild-type plants at maturity, and flowered slightly later than wild type in short-day conditions (Coles, J. P. et al., Plant J. 17: 547-556, 1999). Overexpression of a unique pumpkin 20-oxidase, which produces an inactive GA, has produced plants with a weak GA-deficient phenotype in *Solanum* dulcamara. These plants are semi-dwarfs, have smaller, darker green leaves, flower earlier, and produce more fruit and seed per fruit than wild type plants (Curtis, I. S. et al., Plant J. 23: 329-338, 2000). Overexpression of a bean 2-oxidase in *Arabidopsis* has produced plants with a variety of phenotypes including GA-like dwarfs and semi-dwarfs (Hedden, P. and A. L. Phillips, Trends Plant Sci. 5: 523-530, 2000). The same range of phenotypes was seen when the bean 2-oxidase was overexpressed in wheat (Hedden, P. and A. L. Phillips, Trends Plant Sci. 5: 523-530, 2000). Ectopic expression of a rice 2-oxidase resulted in rice plants which were dwarfed and had darker green, shorter and wider leaf blades, a typical GA-deficient phenotype for rice (Sakamoto, T. et al., Plant Physiol. 125: 1508-1516, 2001).

Genetically altering GA-modifying enzymes has the advantage of providing a means of decreasing chemical usage in plant production, as well as decreasing energy and time expenditures in chemical applications.

BRIEF SUMMARY OF THE INVENTION

The present invention discloses the function, the cDNA sequences, and the expressed amino acid sequences of two genes, the expression of which reduced bioactive GA levels and the height of a plant. The present invention includes various nucleic acid molecules and polypeptides that are related to the two genes and useful in various applications such as detecting the genes, generating antibodies, and generating dwarf plants. The present invention also includes various host cells containing the nucleic acid molecules. The present invention also includes methods of generating dwarf plants using the nucleic acid molecules and the polypeptides described above and the resulted dwarf plants themselves.

It is an object of the present invention to provide a tool to creators of new plant varieties to alter the height of a plant or the size of a specific plant organ.

It is an advantage of the present invention that the two genes are dominant with regard to the dwarf phenotype so that a dwarf transgenic plant is easy to create.

Other objects, advantages and features of the present invention will become apparent from the following specifications and claims.

BRIEF DESCRIPTION OF THE SEVERAL VIEWS OF THE DRAWINGS

FIG. 1 shows alignment of L10 and 69 proteins.
FIG. 2 shows alignment of other GA-modifying enzymes to the L10 and 69 proteins.

DETAILED DESCRIPTION OF THE INVENTION

Set forth below are the cDNA (SEQ ID NO:3 and SEQ ID NO:5) and the deduced amino acid (SEQ ID NO:4 and SEQ ID NO:6) sequences of two plant dwarfism genes, here named L10 and 69, respectively. The names L10 and 69 are for identification purpose only and may be changed to other names (for example, GA_ox_, wherein "_" is a number) to reflect the function of these two genes when the sequences are submitted for publication. When over expressed in a plant, each of these two genes reduced the bioactive GA level and the height of the plant. Prior to the present invention, the genomic DNA sequences (SEQ ID NO:1 and SEQ ID NO:2), but not the cDNA sequences, the amino acid sequences and the function, of these two genes were known. The present invention provides plant breeders and creators a unique tool so as to sculpt the height of a plant to more closely follow the desires of the breeder.

As shown in the examples below, overexpression of either L10 or 69 cause GA-deficiency indicating they are involved in GA degradation, not biosynthesis. L10 and 69 proteins have 44% identity and 54.5% similarity to each other. Both are listed in the database as gibberellin 20-oxidase-like proteins. GA 20-oxidases, however, are involved in biosynthesis, not degradation, although there is one report of a unique pumpkin 20-oxidase whose activity results in an inactive product and causes a dwarf phenotype when overexpressed in certain species (but not in *Arabidopsis*) (Curtis, I. S. et al., Plant J. 23: 329-338, 2000).

By sequence analysis, L10 and 69 do not fit well into any of the three groups of dioxygenases (Tables 1 and 2). In a BLAST search, the GA 20-oxidases from a variety of species show up before any 3β-hydroxylases or 2-oxidases; however, there is only a 28-33% identity between the 20-oxidases and our novel dioxygenases. There is a 24-30% identity between the novel dioxygenases and 3β-hydroxylases or 2-oxidases (Table 1 and 2) from various species. Thus, L10 and 69 dioxygenases do not seem to be significantly more similar to 20-oxidases than to the other dioxygenases (Table 1 and FIG. 2), and their overexpression phenotypes indicate that they are not 20-oxidases or 3β-hydroxylases. 20 oxidases and 3β-hydroxylases are biosynthetic enzymes and their overexpression should therefore lead to taller plants, but overexpression of either L10 or 69 leads to dwarf plants. Thus, if the L10 and 69 dioxygenases are part of a currently recognized class, based upon the overexpression of dwarf phenotype, it is more likely that they are 2-oxidases than either 3β-hydroxylases or 20-oxidases. A complete comparison of the amino acid sequences of all cloned 2-oxidases are shown in Table 2. The unique 20-oxidase from pumpkin is also included. As can be seen in Tables 1 and 2, the L10 and 69 dioxygenases are not as similar to the 2-oxidases as the rest of the 2-oxidases are to each other, even between species. The L10 and 69 dioxygenases are no more similar to the 2-oxidases than the 2-oxidases are to the 20-oxidases or 3β-hydroxylases (Table 1 and 2). Thus, the L10 and 69 dioxygenases are either a new class of dioxygenases or a unique, more distant subgroup of an existing class of dioxygenases.

In one aspect, the present invention relates to a polypeptide including an amino acid sequence that has at least 35%, 40%, 50%, 60%, 70%, 80%, 90%, 95%, 97%, or 99% identity to and over the entire length of that of SEQ ID NO:4, SEQ ID NO:6, SEQ ID NO:4 with conservative substitutions, or SEQ ID NO:6 with conservative substitutions. The present invention also relates to a polypeptide including a novel fragment of the amino acid sequence described above, especially a fragment that is immunogenic or has a biological activity of reducing the bioactive GA level or the height of a plant. Besides the amino acid sequence described above, the polypeptide of the present invention can include a native or non-native amino acid sequence at the N- or C-terminus or both, which will not interfere with the function of the amino acid sequence described above. The flanking native or non-native amino acid sequence can but does not have to be one that assists in purification, detection, or stabilization of the amino acid sequence described above.

As used herein, "percent identity" of the two amino acid sequences or of two nucleic acids is synonymous to "percent homology," which is determined using the algorithm of Karlin and Altschul (Proc. Nati. Acad. Sci. USA 87:2264-2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleotide searches are performed with the NBLAST program, score=100, wordlength=12, to obtain nucleotide sequences homologous to a nucleic acid molecule of the invention. BLAST protein searches are performed with the XBLAST program, score=50, wordlength=3, to obtain amino acid sequences homologous to a reference polypeptide (e.g., SEQ ID NO:4 or SEQ ID NO:6). To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., XBLAST and NBLAST) are used. The referenced programs are available on line from the National Center for Biotechnology Information. National Library of Medicine, National Institute of Health.

Also within the scope of the present invention are polypeptides that bind specifically to an antibody that binds specifically to protein L1.0 or 69.

In another aspect, the present invention relates isolated nucleic acid molecules as described below. An "isolated nucleic acid molecule" used herein is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecules but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transfected cells, and (iii) cell clones, e.g., as these occur in a DNA library such as a cDNA or genomic DNA library. An isolated nucleic acid molecule can be modified or unmodified DNA or RNA, whether fully or partially single-stranded or double-stranded or even triple-stranded. A modified nucleic acid molecule can be chemically or enzymatically induced and can include so-called non-standard bases such as inosine.

An isolated nucleic acid molecule of the present invention is one that includes a polynucleotide having an uninterrupted coding sequence that encodes a polypeptide the amino acid sequence of which is at least 35%, 40%, 50%, 60%, 70%, 80%, 90%, 95%, 97%, or 99% identical to SEQ ID NO:4 or SEQ ID NO:6, a complement of the foregoing, or a novel fragment of any of the foregoing. A preferred nucleic acid molecule includes a polynucleotide having a sequence that is at least 35%, 40%, 50%, 60%, 70%, 80%, 90%, 95%, 97% or 99% identical to SEQ ID NO:3 or SEQ ID NO:5.

The invention also includes nucleic acid molecules that hybridize under stringent hybridization conditions (as defined herein) to all or a portion of the nucleotide sequence represented by SEQ ID NO:3 or its complement, or SEQ ID NO:5 or its complement. The hybridizing portion of the hybridizing nucleic acid molecules is typically at least 15 (e.g., 20, 25, 30, or 50) nucleotides in length. The hybridizing portion of the hybridizing nucleic acid molecules is at least 80%, e.g., at least 95%, or at least 99%, identical to the sequence of a portion or all of a nucleic acid encoding a L10 or 69 polypeptide, or the sequence's complement. Hybridizing nucleic acid molecules of the type described herein can be used, for example, as a cloning probe, a primer (e.g., a PCR primer), or a diagnostic probe. Hybridization of the oligonucleotide probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE).

Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch. Stringent conditions involve hybridizing at 68° C. in 5×SSC/5× Denhardt's solution/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley & Sons, N.Y.) at Unit 2.10.

Isolated nucleic acid molecules of the invention can be obtained by several methods. For example, they can be isolated using procedures which are well known in the art. These include, but are not limited to: (a) hybridization of detectably labeled probes representing all or part of the L10 or 69 gene to genomic or cDNA libraries to detect similar nucleic acid sequences; (b) antibody screening of expression libraries to detect similar structural features; (c) synthesis by the polymerase chain reaction (PCR); and (d) chemical synthesis of a nucleic acid molecule. Sequences for specific coding regions of genes can also be found in GenBank, the National Institutes of Health computer database.

For the identification of isolated nucleic acid molecules using detectably labeled probes, or for the identification of polynucleotide fragments whose complements hybridize to L10 or 69, stringent hybridizing conditions described above can be used. Alternatively, higher stringency conditions can be used. Typically, lower stringency hybridization conditions permit hybridization of related but not identical L10 or 69 gene, and thereby allow identification of the L10 or 69 gene in other species.

In a related aspect, any polynucleotide sequence of the present invention, or an antisense version thereof, can be provided in a vector or genetic construct in a manner known to those skilled in the art. A polypeptide-encoding polynucleotide so provided in a vector can, but need not, be under the transcriptional control of one or more regulatory elements which can include a promoter not natively found adjacent to the polynucleotide such that the encoded polypeptide can be produced when the vector is provided in a compatible host cell or in a cell-free transcription and translation system. Such cell-based and cell-free systems are well known to the skilled artisan. Cells comprising a vector containing a polynucleotide sequence of the invention are themselves within the scope of the invention.

In another related aspect, the present invention encompass a polynucleotide having a nucleotide sequence that encodes a polypeptide the amino acid sequence of which is at least 35%, 40%, 50%, 60%, 70%, 80%, 90%, 95%, 97%, or 99% identical to SEQ ID NO:4 or SEQ ID NO:6, operably linked to a non-native expression control sequence which can include a promoter. Such a polynucleotide of the present invention can be provided in a vector such that the encoded polypeptide can be produced when the vector is provided in a compatible host cell or in a cell-free transcription and translation system. Such cell-based and cell-free systems are well known to the skilled artisan. Cells comprising the vector are themselves within the scope of the invention.

In yet another aspect, the present invention relates to a method of reducing the height of a plant and the resulted dwarf plant. One way to reduce the height of a plant is to increase the transcription or translation rate, or the stability of the mRNA or protein products of the endogenous L10 or 69 gene. Another way to reduce the height of a plant is to make a trangenic plant to express certain isolated nucleic acid molecules of the present invention, which include for example, the L10 or 69 gene of the same or a different species (either the genomic DNA or cDNA of the L10 or 69 gene), a portion of a L10 or 69 gene the protein product of which retains the function of reducing bioactive GA level, and other nucleic acid molecules of the present invention that are effective when expressed in the transgenic plant to cause the transgenic plant to be shorter compared to a non-transgenic plant of the same genetic background.

The examples below showed that expressing the *Arabidopsis* L10 or 69 gene introduced into a *Arabidopsis* plant or the *Arabidopsis* L10 gene introduced into a tobacco plant reduced the height of the *Arabidopsis* or tobacco plant. Identical or similar techniques can be used to express a L10 or 69 gene in other plants species to reduce the height of those species. In addition, this *Arabidopsis* or tobacco plant system can be used to test possible L10 or 69 genes from other plant species and those nucleic acid molecules of the present invention that are effective to cause a transgenic plant to be shorter compared to a non-transgenic plant of the same genetic background.

It should be understood that techniques of plant genetic engineering have been developed to the point where it is now practical to place any genetic construct into almost any useful plant species. The process does, however, still involve some random processes, most notably that insertions of foreign DNA into the genome of plants still occurs at random sites in the plant genome. As a result, in any group of plants emerging from a plant transformation process, the results achieved for the different gene insertion events will vary, sometimes dramatically. For example, for a simple gene insertion of another copy of an endogenous plant gene, many plants produced will have a slightly higher level of activity of the endogenous protein, others will have no measurable change or even a decrease in measurable activity, while a few will have substantial increases in activity levels. However, this variation does not mean stable results cannot be achieved, since the results tend to be consistent generation-to-generation for each specific genetic insertion. Thus the high activity plants have, in effect, a high activity allele that can be transferred by normal mendelian inheritance to their progeny.

To make a transgenic plant, as is known to those of skill in the art, one needs to make a genetic construction capable of expressing an inserted protein coding sequence, whether foreign or endogenous, in a plant. One also needs a method to insert the genetic construction into the plant.

The tools and techniques for making genetic constructions that will express proteins in plants are now widely known. Any genetic construction intended to cause the synthesis in the cells of the plant of a polypeptide or protein must include a sequence of DNA known as a protein coding sequence (can be a genomic DNA or a cDNA), which specifies the sequence of the polypeptide or protein to be produced in the resultant plant. For a protein coding sequence to be expressed in a plant to produce a polypeptide or protein, it must be placed under the control of a plant expressible promoter and be followed by a plant transcriptional terminator sequence, also known as a polyadenlyation sequence. The plant expressible promoter is a promoter which will work in plants, usually either of plant origin or from a plant pathogen like a virus (e.g. Cauliflower mosaic virus) or a bacteria (e.g. *Agrobacterium* promoters like the nopaline synthase promoter). Plant promoters from pathogens tend to be constitutive promoters, meaning that they actually express the protein coding sequence in all of the tissues of the plant at all times. Other plant promoters are known to be tissue specific (e.g. to fruit or to flower) or developmentally specific (e.g. to stage of plant life such as emergent specific or senescent specific), while others are intended to be inducible (e.g. heat shock or metal ion induced promoters). Any of these types of promoters may by used in the practice of this invention depending on the intended affect on the transgenic plant to be produced. For example, a plant with a specific height or stature may be obtained through adjusting the expression level of a transgene by varying promoter strength. One may also use a tissue specific promoter to limit the dwarfing effect such as changing inflorescence architecture, stem elongation, or fruit development without changing any other aspect of the plant.

Several methods have been demonstrated to insert genes into plants to make them transgenic. The most widely used methods, broadly defined, are *Agrobacterium*-mediated transformation or accelerated particle mediated transformation. The various techniques of *Agrobacterium*-mediated plant transformation make use of the natural ability of the plant pathogens of the *Agrobacterium* genus to transfer DNA from a plasmid in the bacteria into the genome of a plant cell. Particle-mediated plant transformation techniques utilize DNA-coated small carrier particles accelerated from a device, often referred to as a gene gun, into the cells of a plant. The full implementation of either approach requires techniques to recover a fully mature, morphologically normal plant from the transformed cells. The techniques often therefore involve either selection or screening protocols to identify which plant cells were transformed and regeneration protocols to recover whole plants from the single transformed plants cells. As mentioned above, these techniques have been worked out for many plant species and many, and perhaps all, of the economically important plant species. Other techniques, such as electroporation have also been used to make transgenic plants. But fundamentally for the invention disclosed here, the particular technique of plant transformation does not matter. Once the plant has been genetically engineered, and a transgenic plant has been created, the method of transformation of the original plant becomes irrelevant. A transgene inserted into the genome of one plant is then fully inheritable by progeny plants of the original genetically engineered plant by normal rules of classical plant breeding. The term transgene is here used to apply to an inserted genetic construction carried in the cells of a target plant. Thus, the term transgenic plant, as used here, refers to a plant that carries such a transgene.

Plants in which a copy of a L10 or 69 gene is introduced may also contain a wild-type (i.e., endogenous) plant height coding region which acts to control the height of the plant. Upon introduction into the genome of a plant, the L10 or 69 gene can act to augment the activity of an endogenous height coding region to make the plant shorter. For instance, a second copy of a height coding region can be introduced into a plant to increase the amount of height reduction L 10 or 69 protein present in the plant.

The present invention also provides a genetically modified plant, characterized as having the phenotypic trait of general dwarfing of the whole plant or dwarfing of a specific plant organ. By this it is meant that the modified plants of the present invention, whether modified by incorporating a L10 or 69 gene expressing a new or additional L10 or 69 protein in the plant, demonstrate a reduced height or size in at least one tissue or organ relative to the same plant without the transgene inserted. Preferably, the dwarfing of the whole transgenic plant or a specific tissue or organ (on average) of the transgenic plant is at least about 20%, more preferably at least about 100%, most preferably at least about 200% in comparison to the same plant without the transgene. Preferably, the genetically modified plant and the same plant without the transgene are grown under the same conditions.

Plants included in the invention are any plants amenable to transformation techniques, including both monocotyledonous and dicotyledonous plants. Examples of monocotyledonous plants include, but are not limited to, vegetables such as asparagus, onions and garlic; cereals such as maize, barley, wheat, rice, sorghum, pearl millet, rye and oats; and grasses such as forage grasses and turfgrasses. Examples of dicotyledonous plants include, but are not limited to, vegetables, feed, and oil crops such as tomato, beans, soybeans, peppers, lettuce, peas, alfalfa, clover, *Brassica* species (e.g., cabbage, broccoli, cauliflower, brussel sprouts, rapeseed, and radish), carrot, beets, eggplant, spinach, cucumber, squash, melons, cantaloupe, sunflowers; fiber crops such as cotton; and various ornamentals such as flowers and shrubs.

In another related aspect, the isolated nucleic acid molecules of the present invention can be used to analyze and determine the pattern of L10 or 69 gene activity of a transgenic or non-transgenic plant as an aid to breeding or creating plants having desired heights.

The above disclosure generally describes the present invention. A more complete understanding can be obtained by reference to the following specific examples which are provided herein for purposes of illustration only and are not intended to limit the scope of the invention.

EXAMPLES

1. Isolation of Mutants that Possessed Altered GA-Metabolism.

*Arabidopsis* was mutagenized by T-DNA derived from *Agrobacterium tumefaciens* to generate plants with altered phenotypes. The mutagenesis was designed to isolate plants that contained dominant phenotypes by use of a T-DNA vector that contained a transcriptional enhancer region (PSKI15 activation vector) (Weigel, D. et al., Plant Physiol. 122: 1003-1013, 2000). Plants were screened in the initial (T1) generation to identify mutant plants that displayed altered inflorescence architecture.

Two mutant plants (Line 10 (L10) and Line 69, (69)) were identified that displayed smaller and darker green leaves, delayed floral induction, and reduced primary inflorescence length (Table 3). These phenotypes are similar to loss-of-function alleles of GA biosynthetic enzymes. When GA levels were directly measured it was found that bioactive GAs in the mutants L10 and 69 were substantially lower than wild-type plants. Bioactive GA (GA4) was measured in wild-type plants at 1.84 ng/g dry weight; whereas, both L10 and 69 plants did not contain detectable levels of GA4. Additionally, other GA forms were also substantially lower in the L10 and 69 lines (Table 4). Both mutant phenotypes could be rescued by the external application of bioactive GA3, which is consistent with the notion that the phenotypes were a result of reduced levels of bioactive GAs.

Heterozygous plants of L10 and 69 were self-pollinated to create a segregating population. A 3:1 ratio of mutant to wild-type plants was observed in the segregating population of both L10 and 69 indicating that both phenotypes are dominant. There are no detectable differences between heterozygous and homozygous phenotypes for either mutant and thus each appears to behave in a fully dominant manner.

The phenotype of the mutants cosegregated with the T-DNA present in the mutants. More than 100 plants from the segregating population were assayed for both the altered GA phenotype and the presence of the T-DNA. All of the plants that displayed the GA-deficient phenotype contained the T-DNA while none of the wild-type plants contained the T-DNA. The probability of this cosegregation occurring randomly is less than 0.00001 and therefore indicated that the T-DNA caused the mutant phenotype seen in the L10 and 69 lines.

2. Cloning of Genes that Caused the L10 and 69 Mutant Phenotypes.

Since the T-DNA cosegregated with the mutant phenotype, it was possible to sequence the genomic DNA near the T-DNA to determine where in the genome the T-DNA was located. A piece of the genomic DNA near the T-DNA from both mutants was sequenced and used to search the *Arabidopsis* data base (which includes sequences from many organisms) available on line from the National Center for Biotechnology Information, National Library of Medicine, National Institute of Health. The search revealed that genomic DNA sequences corresponding to predicted genes were directly adjacent to the enhancer region of the inserted T-DNA in both L10 and 69 plants. These genes were designated L10 and 69, respectively. In the *Arabidopsis* data base, 69 is on BAC F7J7 (accession number AL021960: *Arabidopsis thaliana* DNA chromosome 4, BAC clone F7J7 (ESSA project)). It is number 140 (F7J7.140) on that BAC. The nucleotide sequence is annotated as "similarity to gibberellin C-20 oxidase, *Oryza sativa*, PATCHX:G1854637." The predicted protein (CAA17539.1) is annotated as "gibberellin 20-oxidase-like protein." L10 is on BAC F8A12 (accession number AC079284: *Arabidopsis thaliana* chromosome 1 BAC F8A12 genomic sequence, complete sequence). It is number 18 (F8A12.18) on that BAG. The nucleotide sequence is annotated as "similar to gibberellin 20 oxidase (Triticum aestivum) GI:2222796." The predicted protein (AAG50945.1) is annotated as "gibberellin 20-oxidase, putative."

Based on the above information, we have determined the cDNA sequences for L10 and 69 as SEQ ID NO:3 and SEQ ID NO:5, respectively.

Reverse-transcription-based PCR was used to determine the expression levels of the L10 and 69 gene in the two mutants. Both L10 and 69 plants had substantially increased mRNA levels of their respective enzymes. This observation is consistent with the hypothesis that the phenotypes of the mutants were due to activation of gene expression caused by the enhancer region of the T-DNA.

3. Ectopic Expression of L10 and 69 in *Arabidopsis*.

To test the hypothesis that the L10 and 69 phenotypes were due to the activation of the respective GA-modifying genes, L10 and 69 were constitutively overexpressed. The genomic region of the respective genes was cloned into a vector that contained a cauliflower mosaic virus 35S promoter (35S) that provides constitutive mRNA expression in most plant tissues.

These new vectors that contained the 35S:L10 or 35S:69 constructs were transformed into wild-type *Arabidopsis*. First generation transformed plants were screened for phenotypes similar to the respective initial L10 or 69 lines. Approximately half of the transformed plants displayed phenotypes similar or identical to that of the initially isolated L10 or 69 lines, respectively. Thus, increased expression of the GA-modifying genes was sufficient to cause the alterations in plant growth and stature that were seen in the initially isolated mutant lines. This data confirmed that the activation of the GA-modifying genes near the T-DNA inserts had caused the dominant GA-deficient phenotypes. In addition to the 35S-driven genomic clones, the cDNAs for each of the L10 and 69 lines were also placed under the transcriptional control of the 35S promoter and were found to also cause a dwarf, GA-deficient-like phenotype. This indicates that the cDNAs are functional and sufficient for the purposes of altering GA metabolism to produce the aforementioned phenotypes.

4. Ectopic Expression of L10 Functions in Tobacco to Produce GA-Deficient-Like Plants.

Introduction of the 35S:L10 or 355:69 into wild-type tobacco (Wisconsin 38) produces plants that appear to be deficient in bioactive GAs. Many phenotypic changes are similar to the phenotypic changes in *Arabidopsis*. For example, the leaves are smaller and darker green, plant height is reduced, and internode distance is shortened (Table 5). The 35S:L10 and 355:69 tobacco plants and the wild-type plant had similar seed yield.

5. Sequence Alignments of L10 and 69 to GA-Modifying Enzymes.

L10 and 69 are more similar to each other than to any other protein in the *Arabidopsis* database. When L10 is used to BLAST search the *Arabidopsis* database of proteins, the closest match to L10 is 69. Likewise, when 69 is used to search the database L10 is the closest match to 69. This implies that L10 and 69 may define a group of GA-modifying enzymes that may be functionally distinct from other GA-modifying enzymes (Tables 1 and 2). An alignment of L10 to 69, depicted in FIG. 1, reveals that there is 44% identity and 54.5% similarity shared by the two proteins. In FIG. 1, lines denote identity and colons and periods denote degree of similarity.

An alignment of L10 and 69 to AtGA2ox1, AtGA2ox2, AtGA2ox3, AtGA20ox1, GA5 (a 20-oxidase), and GA4 (a 3β-hydroxylase), as depicted in FIG. 2, reveals that these enzymes contain regions of similarity (see also Table 2). In FIG. 2, amino acid residues that are identical with 69 protein are designated by a black box surrounding the amino acid residue and similarities in amino acid residues to 69 proteins are denoted by gray shading around residues. However, L10 and 69 contain unique regions that are similar to each other but show little or no relatedness to the other GA-modification enzymes. The two most prominent examples of this are the sequence from L10 at amino acid 115 through 137 and the carboxy terminus of L10 and 69 defined by the L10 protein sequence at amino acid 304 through 335 (FIGS. 1 and 2).

TABLE 1

Percent identity between novel dioxygenases and other known Arabidopsis dioxygenases (Numbers in the table are percent identity. Thick lines separate the groups of dioxygenases and the values under these lines illustrate the high percent of identity within each group. All of the dioxygenases are from Arabidopsis. At 2ox1-3 are the three cloned 2-oxidases (accession nos. AJ32435, AJ132436, and AJ132437). At20ox1-3 are three 20-oxidases (accession nos. X83379, X83380, and X83381). At 3ox1-2 are two 3β-hydroxylases (accession nos. L37126 and T51691)).

|  | L10 | 69 | At 2ox1 | At 2ox2 | At 2ox3 | At 20ox1 | At 20ox2 | At 20ox3 | At 3ox1 | At 3ox2 |
|---|---|---|---|---|---|---|---|---|---|---|
| L10 | — | 44 | 27 | 25 | 25 | 32 | 31 | 31 | 28 | 28 |
| 69 |  | — | 29 | 26 | 27 | 32 | 30 | 31 | 29 | 25 |
| At 2ox1 |  |  | — | 55 | 53 | 31 | 29 | 29 | 31 | 32 |
| At 2ox2 |  |  |  | — | 69 | 28 | 28 | 28 | 34 | 33 |
| At 2ox3 |  |  |  |  | — | 27 | 30 | 28 | 33 | 32 |
| At 20ox1 |  |  |  |  |  | — | 73 | 61 | 31 | 29 |
| At 20ox2 |  |  |  |  |  |  | — | 64 | 32 | 30 |
| At 20ox3 |  |  |  |  |  |  |  | — | 32 | 32 |
| At 3ox1 |  |  |  |  |  |  |  |  | — | 74 |
| At 3ox2 |  |  |  |  |  |  |  |  |  | — |

TABLE 2

Percent identity between the L10 and 69 dioxygenases and other known GA-degrading enzymes (Numbers in the table are percent identity. A thick line separates the known 2-oxidases. L10 and 69 are our two novel dioxygenases. At 2ox1-3 are the three 2-oxidases in Arabidopsis (accession nos. AJ132435, AJ132436, and AJ132437). Rice 2ox is the 2-oxidase from Oryza sativa (Sakamota, 2001). Bean 2ox is the 2-oxidase from Phaseolus coccineus (accession no. AJ132438). Pea 2ox1-2 are the two 2-oxidases from Pisum sativum (accession nos. AF1009541 and AF056935). Pumpkin 20ox is the unique 20-oxidase from Cucurbita maxima (accession no. AAB64345)).

|  | L10 | 69 | At 2ox1 | At 2ox2 | At 2ox3 | Rice 2ox | Bean 2ox | Pea 2ox1 | Pea 2ox2 | Pumpkin 20ox |
|---|---|---|---|---|---|---|---|---|---|---|
| L10 | — | 44 | 27 | 25 | 25 | 24 | 26 | 29 | 25 | 29 |
| 69 |  | — | 29 | 26 | 27 | 23 | 25 | 28 | 26 | 30 |
| At 2ox1 |  |  | — | 55 | 53 | 38 | 57 | 47 | 55 | 29 |
| At 2ox2 |  |  |  | — | 69 | 37 | 63 | 45 | 56 | 32 |
| At 2ox3 |  |  |  |  | — | 38 | 56 | 47 | 55 | 26 |
| Rice 2ox |  |  |  |  |  | — | 39 | 46 | 41 | 28 |
| Bean 2ox |  |  |  |  |  |  | — | 50 | 59 | 30 |
| Pea 2ox1 |  |  |  |  |  |  |  | — | 47 | 27 |
| Pea 2ox2 |  |  |  |  |  |  |  |  | — | 27 |
| Pumpkin 20ox |  |  |  |  |  |  |  |  |  | — |

TABLE 3

Characterization of the Mutant Phenotypes of L10 and 69 Lines.

|  | Wild-Type | L10 | 69 | 35S::L10 | 35S::69 | $GA_3$-treated L10 | $GA_3$-treated 69 |
|---|---|---|---|---|---|---|---|
| Flowering Time LD (Number of Leaves) | 8 | 17 | 15 | 16 | 15 | 8 | 8 |
| Height cm | 47 | 7.2 | 9.4 | 8.2 | 9.6 | 30 | 30 |
| Number of Flowering Branches | 41 | 77 | 84 | >100 | >100 | 65 | 65 |
| Internode Length mm | 8.9 | 1.8 | 2.3 | 2.4 | 2.6 | 7 | 7 |

TABLE 4

Abundance of GAs Present in Wild Type and Mutant Lines

| GAs | Ws (wild type) | 69 | L10 |
|---|---|---|---|
| Non-13-Hydroxylated: |  |  |  |
| $GA_{24}$ | 51.8 | 0.23 | 0.06 |
| $GA_9$ | 1.01 | 0.05 | 0.02 |
| $GA_4$ | 1.84 | ND | ND |
| 13-Hydroxylated: |  |  |  |
| $GA_{53}$ | 6.43 | 0.30 | 0.39 |
| $GA_{44}$ | 0.79 | ND | ND |
| $GA_{19}$ | 9.29 | 0.09 | 0.02 |
| $GA_{20}$ | 0.19 | ND | ND |
| $GA_1$ | 0.12 | 0.02 | ND |

(All values are in ng/g dry weight. ND = not detectable).

TABLE 5

Phenotypic Alterations in Tobacco with Ectopic Expression of L10.

| Characteristic | Wild Type | 35S::L10 |
|---|---|---|
| Leaf Length in cm | 32 | 10 |
| Height in cm | 8.5 | 2.5 |
| Internode distance in cm | 0.7 | 0.2 |

The complete disclosures of all publications that are cited herein are hereby incorporated by reference as if individually incorporated. It is also understood that, given the limitations of the state of the art, occasional sequence errors or deletions may occur without affecting the usefulness of the data presented. Various modifications and alterations of this invention will become apparent to those skilled in the art without departing from the scope and spirit of this invention, and it should be understood that this invention is not to be unduly limited to the illustrative embodiments set forth herein, but rather is to be construed to be of spirit and scope defined by the appended claims.

We claim:

1. An isolated nucleic acid molecule comprising a polynucleotide having an uninterrupted coding sequence that encodes the amino acid sequence of SEQ ID NO:6.

2. An isolated nucleic acid molecule comprising a polynucleotide having the nucleotide sequence of SEQ ID NO:5.

3. A The nucleic acid construct comprising:
a polynucleotide has having a nucleotide sequence that encodes SEQ ID NO:6, the polynucleotide being operably linked to a heterologous plant expressible promoter, wherein expression of the polynucleotide in a transgenic plant causes the plant to be shorter compared to a non-transgenic plant of the same genetic background.

4. A transgenic plant comprising in its genome the nucleic acid construct of claim 3 wherein the polynucleotide is expressed in the plant.

5. The transgenic plant of claim 4, wherein the transgenic plant is at least 20% shorter than a non-transgenic plant of the same genetic background while being grown under the same conditions.

6. A seed of the transgenic plant of claim 4 wherein the seed contains the same nucleic acid construct as the transgenic plant.

* * * * *

UNITED STATES PATENT AND TRADEMARK OFFICE
CERTIFICATE OF CORRECTION

PATENT NO. : 7,420,102 B2  
APPLICATION NO. : 11/152892  
DATED : September 2, 2008  
INVENTOR(S) : Richard M. Amasino et al.

Page 1 of 1

It is certified that error appears in the above-identified patent and that said Letters Patent is hereby corrected as shown below:

In the Specifications

Column 5, line 12     "L1.0" should be --L10--

Column 9, line 50     "PSKI15" should be --pSKI15--

Column 10, line 45     "BAG" should be --BAC--

In the Claims

Column 41, line 8, claim 3     "has having" should be --having--

Signed and Sealed this  
Fourth Day of February, 2014

Michelle K. Lee  
*Deputy Director of the United States Patent and Trademark Office*

```
                              SEQUENCE LISTING

<160> NUMBER OF SEQ ID NOS: 12

<210> SEQ ID NO 1
<211> LENGTH: 2171
<212> TYPE: DNA
<213> ORGANISM: Arabidopsis

<400> SEQUENCE: 1
atggcttctc aacctccctt taagacaaat ttctgctcga ttttcggaag ctcatttcca      60
aattcaacta gtgagagcaa tacaaacaca tcaactatcc aaacctcagg cataaagctt     120
cctgtgatcg atctcagcca tctaactagt ggtgaggagg tcaaacgcaa aagatgtgtg     180
aaacaaatgg ttgcagctgc gaaagagtgg ggatttttc  aaattgtgaa ccatggaatt     240
cccaaagacg tctttgagat gatgctcctc gaagagaaga aactctttga ccaacctttt     300
tctgtgaaag tcagagaacg tttttcggac ttatcgaaga atagttaccg ttggggaaac     360
cctagcgcca cttctcccgc tcagtactcc gtttcggaag cgtttcacat cattctttca     420
gaggtttcaa ggatttctga tgatcgcaac aacctcaggt tttttaatta taggattttt     480 atcttttattg attgaattct gtctcatgaa acccctaattc ttgaattgtc gtagttgtt       540 cttttaatta taattgactc aactgatatc gtttcaggga aagttctta  gccagtcata     600 ctcgtttcc  cttcagtttc atcaatcata attttctaga tatcttttat gaaattcttg      660
cgagtatata gattttaaat atttggagtg aaatttggtt ttgctgaaga tttcaatttt     720
tggaatgaaa ttgttatggg tctttggaag atcaagcaag gttcacatgc ttgtaatata     780
gtagtattat agaaacactt ataaatcttt tatgtttaag gaaaactttc atacagttca     840
tatatagaga tatattgtag ttatacatac aaaataaaaa aaaatacaag atcataaatc     900
attatatact atatatagat agatgagtaa ccgttacata attaatttct attttctttt     960
tacagaacaa tcgttgaaac gtatgtgcaa gagatagctc gagtggcaca aatgatatgt    1020
gaaatactgg ggaaacaagt gaacgtgagt tcggagtatt tcgaaaacat ttttgagctt    1080
gaaaacagtt ttctaaggct caataagtac catcctagtt tttttggttc tgaagtgttt    1140
ggtttggttc ctcataccga tacaagtttt ctcactatac tctctcaaga tcaaatcgga    1200
gggttagaat tggaaaataa tggacaatgg atcagcgtaa aaccttgctt ggaagcccttt    1260 acagtcaaca ttggggatat gtttcaggta attacttcta cccttttgatt ttcaacgttc    1320 aagtccatta aggttagcta ttgccctgta tcattttttca acagcgaact attaattagt    1380
tctatgattc taaagcgtat atgacttaga ataaagcaaa tcctaaaact tcagtagaag    1440
tttttctggt atattatttt atatatatag gtaaaatgtc acgagagata atgttaatta    1500
atacaaaaat gttaagaaac atatgcttaa ttaggcgcca caaaaaaaaa attgtgttat    1560
caattgtttc tgttgttcaa taaaattctg aatatagtta tgaagtaatt gtataaatcc    1620
tttattttat cgaattggtt tctctatgaa ctatattggt cataagttca ggggaaaccc    1680
tagaaaatta tcaagggcca agcttttgca tgagcttcga tctggtgcct aacatatatt    1740
agataagatc tactgattta aattttaata tatattgcta atcattctca aagaacttct    1800
ttgattttat ttataagaaa gagatgacag ttgaaaccaa cctatattac aactcaaatt    1860
aacgctaatg tctttgatag acaaatatat aaatcgtata tatatatttt gcaagctaat    1920
```

```
tattttcatg tatgctatag gcactgagta atggagtgta ccaaagcgtg agacatagag   1980
tgatttctcc agcaaatatc gagaggatgt caatagcttt cttcgtatgt ccttatctcg   2040
aaactgagat cgattgcttt gggtatccaa agaagtatag aagattcagt ttcagagagt   2100
acaaagagca gagtgaacat gatgttaaag aaactggtga taaggtaggc ttgtccaggt   2160
ttctcatttg a                                                        2171

<210> SEQ ID NO 2
<211> LENGTH: 3861
<212> TYPE: DNA
<213> ORGANISM: Arabidopsis

<400> SEQUENCE: 2
agatcttctc atggatccac cattcaacga aatatacaat aaccttttgt ataatcagat     60
cacaaagaaa gataacgatg tttctgaaat acccttttagc ttctcagtca cagccgtcgt   120
cgaggaggtg gagcttcctg tgattgacgt cagccgtttg attgatggag ccgaggagga   180
gagagagaaa tgtaaggaag cgattgcgag agcttcgagg gagtggggat ttttcaagt    240 gataaaccat ggaatatcaa tggatgtgtt ggagaagatg agacaagagc aaattagggt   300
ctttagagag cctttttgaca agaaaagtaa gtcggagaaa tttccgccg ggagttaccg   360 gtggggaacg ccgtcagcca cttctatccg gcagctttct tggtcagaag cttttcatgt   420
tcccatgaca gatatttctg acaacaagga ctttactact ctcaggtaca caaatattgt   480
tatcaattac atttttttag aattaattta cttattaaac ttaattatt gaaaaaatat    540 gtggagaatt atcccaataa caagatgtaa attaaaatac aactttaccct ttcttttggt  600 taagttacct tctaaacaac tagtgttttg aggattagta agtaaatttt aatgacatat   660
ataatgatac aactatagta ttaattaata tcaagttttt gactataagt aacactattt   720
gcaaagaaaa ttaattaatt agtcaaagat tagacatggg agacaaacac agttttaat    780 tcagtatatg gtggttttga agcatataat agagtgttgt catttatatt taattaataa   840
tagttttgga tattttagaa atttaatcct agaaaataaa gttgttgggc attgggtcaa   900 agattttattc cccatatctc atgcgtttct atgtttttcca tttttaatac tattttttgaa 960 tacgtctaat tttgggatag caagttggca tgtgaaatac aatgaataaa taacaatat   1020 taagactttt caaacaaaaa taaaatatta tgtatttgga aaatatataa gaaataaatc  1080
ttaacgtaga ttttttttgt ttgttaaaga caatcttaa gatagttaat taaactctag   1140
ctaacttttt ttaagatacc tctaatgttg ttatttattc tttgattctt cgtattcgta   1200
ggaacttcgt caacttcaaa ttcttttaaca tgctagaaaa tataatggac ttcttagaat  1260
taatattctg cattagctgc gccgcggaat gattttttta tgaaacaaac ctttttattg   1320
ttatatatcc aaacaatcat cattttttag tagttgttgt cagatttttt caatagaaaa   1380
tgggatttag accaactgat gattttggtc ggttttgtc gggagaaata atcgaaaacc    1440
attaaccaac tcatggttcc gaaaaaaaaa acccatcaac caactcatta gaagacataa    1500
gttgcttttc aaaacaatat ataaacatta tactacgagt ctgcgaacgt ttatatctga   1560
aaactttcaa acaattaaca cgcctataca taactggaat caaactaacc attttacatt    1620
tacaatatct tagttatatc tcttttttttt ttgtccaaaa gagattatgt atcataactt   1680
ttttcatatg tgtgttcaat taagaatttt tgaataacct ttaccaaaaa aaagaaaag    1740 aattttctca aataaaattt tagttactc agaacctcta aaaacaagct aggtacgatc   1800
```

-continued

| | |
|---|---|
| tagaaacata tagtacacac tatttgtgta taatacataa ctacagtact atatggtgag | 1860 |
| aaaagaaagg aagagtcacg agaaaactgt ctgtttggca aatgagggat aatggaaggg | 1920 |
| aagaagaagt actcggacat gccaggctag ctagctatat ataaatacac acgtatataa | 1980 |
| attatcttgt gatcagtgtg tactaatgtg tgctggaatc tgtacacatt cttatatgta | 2040 |
| catatgtatt tgcatgcatg tggttgtctt acacatcttt atgcattgtt tcagcttctg | 2100 |
| tgcgtgtttg tgtatgtgtg accacatacc gttgttactt ttcatagttg gcgttctctt | 2160 |
| gataagtcac tgttagtgtg gcaatttgac aataaaatct aaaatgttat taattataac | 2220 |
| accccaattc aatatatata tatatacaca taagaaaaa tgtatgtgga aagttcaaac | 2280 |
| tataatccat gagataatag aaatatagat ccgaattta ttatggtttt acagtgatct | 2340 |
| aatatattgt agacaaaaat ggtttagaaa acacttgaat gcaaatgcct aaaaaggcta | 2400 |
| aaacacatgc atcaccgatc attttgctaa aatttcagtt gaaaataaga tgcaatactt | 2460 |
| tattttttaaa aaataaaatt agagatgaat ttttttttgta ttaattttttt ttaataactt | 2520 |
| ttgatcctta atctctttga aaaaacaaa acaaaacaaa acatgtataa tccctttatt | 2580 |
| accgtctggt atttatatat tagactgacc ggattgtggt atagtcttcc aaatgtccaa | 2640 |
| tactttctag accgagctaa tccaaccgga tgataaagtg aatagagttc atcattcaaa | 2700 |
| tgtcaaatga actatagtct atatacatag atgcatgcat ataaagagta tccaaaaaga | 2760 |
| gaaataatat agaagactca aaattggaaa aagggtccca tgttcctaac aggtaggaga | 2820 |
| tatctctatc atagagaaac aatggatcgt acacgtacac gtacatctcc tctcaacctg | 2880 |
| attcataccc attttccttt ctctactcgt ccttgattta gtctcttggg acccttctcc | 2940 |
| attatatctc acatgtctct caaacttcct gccatttcac ctccttacat gtcaatttgc | 3000 |
| ttcgatcacc ttaattatat tatgggcatg ttataatgtt cttatcttct aatttgtttc | 3060 |
| acagctcaac aatggagaaa tttgcttcgg aatcagaggc attagcatat atgttggcag | 3120 |
| aggttcttgc agaaaaatct ggacaaaatt caagtttctt caaagaaaac tgtgtgagaa | 3180 |
| atacatgtta tctaaggatg aaccgatatc caccttgtcc caaaccatcg gaggtgtacg | 3240 |
| gattaatgcc acacacggac agtgatttcc tcacaatctt gtatcaagat caagtcggag | 3300 |
| gactccaact tatcaaagac aatagatgga tcgctgttaa acctaatcct aaagctctca | 3360 |
| ttatcaatat tggtgactta tttcaggtaa ttgagctttt attatgtcat tctaccatta | 3420 |
| ccattatatc attatccgga gcttacaaat tagtttggta ttttatgttt tgatatggtt | 3480 |
| tggaaggatt taaacaattt gttcatacgc atgcatgatc aataattaaa aatgtggatt | 3540 |
| tcttataaag ataacatcta aggcaatgta ttaaaaatgt cttaaatta ctagattgta | 3600 |
| cttatatatg tgtttggtta ggcatggagc aatggcatg acaaaagtgt tgaacaccgt | 3660 |
| gtgatgacga acccaaaggt ggagagattc tcaacggctt attttatgtg tccatcatac | 3720 |
| gacgccgtta tagagtgttc aagtgatcgt cctgcttata gaaatttcag cttcagagaa | 3780 |
| ttcagacaac aagttcaaga agatgttaag aagtttggtt taaagttgg ccttcctagg | 3840 |
| ttccttaatc acgtctacta a | 3861 |

<210> SEQ ID NO 3
<211> LENGTH: 1011
<212> TYPE: DNA
<213> ORGANISM: Arabidopsis
<220> FEATURE:
<221> NAME/KEY: CDS
<222> LOCATION: (1)..(1008)

<400> SEQUENCE: 3

```
atg gct tct caa cct ccc ttt aag aca aat ttc tgc tcg att ttc gga      48
Met Ala Ser Gln Pro Pro Phe Lys Thr Asn Phe Cys Ser Ile Phe Gly
 1               5                  10                  15 agc tca ttt cca aat tca act agt gat agc aat aca aac aca tca act      96
Ser Ser Phe Pro Asn Ser Thr Ser Asp Ser Asn Thr Asn Thr Ser Thr
             20                  25                  30 atc caa acc tca ggc tta aag ctt cct gtg atc gat ctc agc cat cta     144
Ile Gln Thr Ser Gly Leu Lys Leu Pro Val Ile Asp Leu Ser His Leu
         35                  40                  45 act agt ggt gag gag gtc aaa cgc aaa aga tgt gtg aaa caa atg gtt     192
Thr Ser Gly Glu Glu Val Lys Arg Lys Arg Cys Val Lys Gln Met Val
 50                  55                  60 gca gct gcg aaa gag tgg gga ttt ttt caa att gtg aac cat gga att     240
Ala Ala Ala Lys Glu Trp Gly Phe Phe Gln Ile Val Asn His Gly Ile
 65                  70                  75                  80 ccc aaa gac gtc ttt gag atg atg ctc ctc gaa gag aag aaa ctc ttt     288
Pro Lys Asp Val Phe Glu Met Met Leu Leu Glu Glu Lys Lys Leu Phe
                 85                  90                  95 gac caa cct ttt tct gtg aaa gtc aga gaa cgt ttt tcg gac tta tcg     336
Asp Gln Pro Phe Ser Val Lys Val Arg Glu Arg Phe Ser Asp Leu Ser
            100                 105                 110 aag aat agt tac cgt tgg gga aac cct agc gcc act tct ccc gct cag     384
Lys Asn Ser Tyr Arg Trp Gly Asn Pro Ser Ala Thr Ser Pro Ala Gln
        115                 120                 125 tac tcc gtt tcg gaa gcg ttt cac atc att ctt tca gag gtt tca agg     432
Tyr Ser Val Ser Glu Ala Phe His Ile Ile Leu Ser Glu Val Ser Arg
    130                 135                 140 att tct gat gat cgc aac aac ctc aga aca atc gtt gaa gcg tat gtg     480
Ile Ser Asp Asp Arg Asn Asn Leu Arg Thr Ile Val Glu Ala Tyr Val
145                 150                 155                 160 caa gag ata gct cga gtg gca caa atg ata tgt gaa ata ctg ggg aaa     528
Gln Glu Ile Ala Arg Val Ala Gln Met Ile Cys Glu Ile Leu Gly Lys
                165                 170                 175 caa gtg aac gtg agt tcg gag tat ttc gaa aac att ttt gag ctt gaa     576
Gln Val Asn Val Ser Ser Glu Tyr Phe Glu Asn Ile Phe Glu Leu Glu
            180                 185                 190 aac agt ttt cta agg ctc aat aag tac cat cct agt gtt ttt ggt tct     624
Asn Ser Phe Leu Arg Leu Asn Lys Tyr His Pro Ser Val Phe Gly Ser
        195                 200                 205 gaa gtg ttt ggt ttg gtt cct cat acc gat aca agt ttt ctc act ata     672
Glu Val Phe Gly Leu Val Pro His Thr Asp Thr Ser Phe Leu Thr Ile
    210                 215                 220 ctc tct caa gat caa atc gga ggg tta gaa ttg gaa aat aat gga caa     720
Leu Ser Gln Asp Gln Ile Gly Gly Leu Glu Leu Glu Asn Asn Gly Gln
225                 230                 235                 240 tgg atc agc gta aaa cct tgc ttg gaa gcc ctt aca gtc aac att ggg     768
Trp Ile Ser Val Lys Pro Cys Leu Glu Ala Leu Thr Val Asn Ile Gly
                245                 250                 255 gat atg ttt cag gca ctg agt aat gga gtg tac caa agc gtg aga cat     816
Asp Met Phe Gln Ala Leu Ser Asn Gly Val Tyr Gln Ser Val Arg His
            260                 265                 270 aga gtg att tct cca gca aat atc gag agg atg tca ata gct ttc ttc     864
Arg Val Ile Ser Pro Ala Asn Ile Glu Arg Met Ser Ile Ala Phe Phe
        275                 280                 285 gta tgt cct tat ctc gaa act gag atc gat tgc ttt ggg tat cca aag     912
Val Cys Pro Tyr Leu Glu Thr Glu Ile Asp Cys Phe Gly Tyr Pro Lys
    290                 295                 300 aag tat aga aga ttc agt ttc aga gag tac aaa gag cag agt gaa cat     960
```

```
Lys Tyr Arg Arg Phe Ser Phe Arg Glu Tyr Lys Glu Gln Ser Glu His
305                 310                 315                 320 gat gtt aaa gaa act ggt gat aag gta ggc ttg tcc agg ttt ctc att      1008
Asp Val Lys Glu Thr Gly Asp Lys Val Gly Leu Ser Arg Phe Leu Ile
                325                 330                 335 tga                                                                   1011

<210> SEQ ID NO 4
<211> LENGTH: 336
<212> TYPE: PRT
<213> ORGANISM: Arabidopsis

<400> SEQUENCE: 4

Met Ala Ser Gln Pro Pro Phe Lys Thr Asn Phe Cys Ser Ile Phe Gly
 1               5                  10                  15

Ser Ser Phe Pro Asn Ser Thr Ser Asp Ser Asn Thr Asn Thr Ser Thr
             20                  25                  30

Ile Gln Thr Ser Gly Leu Lys Leu Pro Val Ile Asp Leu Ser His Leu
         35                  40                  45

Thr Ser Gly Glu Glu Val Lys Arg Lys Arg Cys Val Lys Gln Met Val
     50                  55                  60

Ala Ala Lys Glu Trp Gly Phe Phe Gln Ile Val Asn His Gly Ile
 65                  70                  75                  80

Pro Lys Asp Val Phe Glu Met Met Leu Leu Glu Lys Lys Leu Phe
                 85                  90                  95

Asp Gln Pro Phe Ser Val Lys Val Arg Glu Arg Phe Ser Asp Leu Ser
            100                 105                 110

Lys Asn Ser Tyr Arg Trp Gly Asn Pro Ser Ala Thr Ser Pro Ala Gln
        115                 120                 125

Tyr Ser Val Ser Glu Ala Phe His Ile Ile Leu Ser Glu Val Ser Arg
    130                 135                 140

Ile Ser Asp Asp Arg Asn Asn Leu Arg Thr Ile Val Glu Ala Tyr Val
145                 150                 155                 160

Gln Glu Ile Ala Arg Val Ala Gln Met Ile Cys Glu Ile Leu Gly Lys
                165                 170                 175

Gln Val Asn Val Ser Ser Glu Tyr Phe Glu Asn Ile Phe Glu Leu Glu
            180                 185                 190

Asn Ser Phe Leu Arg Leu Asn Lys Tyr His Pro Ser Val Phe Gly Ser
        195                 200                 205

Glu Val Phe Gly Leu Val Pro His Thr Asp Thr Ser Phe Leu Thr Ile
    210                 215                 220

Leu Ser Gln Asp Gln Ile Gly Gly Leu Glu Leu Glu Asn Asn Gly Gln
225                 230                 235                 240

Trp Ile Ser Val Lys Pro Cys Leu Glu Ala Leu Thr Val Asn Ile Gly
                245                 250                 255

Asp Met Phe Gln Ala Leu Ser Asn Gly Val Tyr Gln Ser Val Arg His
            260                 265                 270

Arg Val Ile Ser Pro Ala Asn Ile Glu Arg Met Ser Ile Ala Phe Phe
        275                 280                 285

Val Cys Pro Tyr Leu Glu Thr Glu Ile Asp Cys Phe Gly Tyr Pro Lys
    290                 295                 300

Lys Tyr Arg Arg Phe Ser Phe Arg Glu Tyr Lys Glu Gln Ser Glu His
305                 310                 315                 320

Asp Val Lys Glu Thr Gly Asp Lys Val Gly Leu Ser Arg Phe Leu Ile
                325                 330                 335
```

<210> SEQ ID NO 5
<211> LENGTH: 1017
<212> TYPE: DNA
<213> ORGANISM: Arabidopsis
<220> FEATURE:
<221> NAME/KEY: CDS
<222> LOCATION: (1)..(1014)

<400> SEQUENCE: 5

| | | | | | | | | | | | | | | | | |
|---|---|---|---|---|---|---|---|---|---|---|---|---|---|---|---|---|
| atg | gac | cca | cca | ttc | aac | gaa | ata | tac | aat | aac | ctt | ttg | tat | aat | cag | 48 |
| Met | Asp | Pro | Pro | Phe | Asn | Glu | Ile | Tyr | Asn | Asn | Leu | Leu | Tyr | Asn | Gln | |
| 1 | | | | 5 | | | | | 10 | | | | | 15 | | |
| atc | aca | aac | aaa | gaa | aac | gat | gtt | tct | gaa | ata | ccc | ttt | agc | ttc | tcc | 96 |
| Ile | Thr | Asn | Lys | Glu | Asn | Asp | Val | Ser | Glu | Ile | Pro | Phe | Ser | Phe | Ser | |
| | | | 20 | | | | | 25 | | | | | 30 | | | |
| gtc | aca | gcc | gtc | gtc | gag | gag | gtg | gag | ctt | cct | gtg | att | gac | gtc | agc | 144 |
| Val | Thr | Ala | Val | Val | Glu | Glu | Val | Glu | Leu | Pro | Val | Ile | Asp | Val | Ser | |
| | | 35 | | | | | 40 | | | | | 45 | | | | |
| cgt | ttg | att | gat | gga | gcc | gag | gag | gag | aga | gag | aaa | tgt | aag | gaa | gcg | 192 |
| Arg | Leu | Ile | Asp | Gly | Ala | Glu | Glu | Glu | Arg | Glu | Lys | Cys | Lys | Glu | Ala | |
| | 50 | | | | | 55 | | | | | 60 | | | | | |
| att | gcg | aga | gct | tcg | agg | gag | tgg | gga | ttt | ttt | caa | gtg | ata | aac | cat | 240 |
| Ile | Ala | Arg | Ala | Ser | Arg | Glu | Trp | Gly | Phe | Phe | Gln | Val | Ile | Asn | His | |
| 65 | | | | | 70 | | | | | 75 | | | | | 80 | |
| gga | ata | tca | atg | gat | gtg | ttg | gag | aag | atg | aga | caa | gag | caa | att | agg | 288 |
| Gly | Ile | Ser | Met | Asp | Val | Leu | Glu | Lys | Met | Arg | Gln | Glu | Gln | Ile | Arg | |
| | | | 85 | | | | | 90 | | | | | 95 | | | |
| gtc | ttt | aga | gag | cct | ttt | gac | aag | aaa | agt | aag | tcg | gag | aaa | ttt | tcc | 336 |
| Val | Phe | Arg | Glu | Pro | Phe | Asp | Lys | Lys | Ser | Lys | Ser | Glu | Lys | Phe | Ser | |
| | | | 100 | | | | | 105 | | | | | 110 | | | |
| gcc | ggg | agt | tac | cgg | tgg | gga | acg | ccg | tca | gcc | act | tct | atc | cgg | cag | 384 |
| Ala | Gly | Ser | Tyr | Arg | Trp | Gly | Thr | Pro | Ser | Ala | Thr | Ser | Ile | Arg | Gln | |
| | | 115 | | | | | 120 | | | | | 125 | | | | |
| ctt | tct | tgg | tca | gaa | gct | ttt | cat | gtt | ccc | atg | aca | gat | att | tct | gac | 432 |
| Leu | Ser | Trp | Ser | Glu | Ala | Phe | His | Val | Pro | Met | Thr | Asp | Ile | Ser | Asp | |
| | 130 | | | | | 135 | | | | | 140 | | | | | |
| aac | aag | gac | ttt | act | act | ctc | agc | tca | aca | atg | gag | aaa | ttt | gct | tcg | 480 |
| Asn | Lys | Asp | Phe | Thr | Thr | Leu | Ser | Ser | Thr | Met | Glu | Lys | Phe | Ala | Ser | |
| 145 | | | | | 150 | | | | | 155 | | | | | 160 | |
| gaa | tca | gag | gca | tta | gca | tat | atg | ttg | gca | gag | gtt | ctt | gca | gaa | aaa | 528 |
| Glu | Ser | Glu | Ala | Leu | Ala | Tyr | Met | Leu | Ala | Glu | Val | Leu | Ala | Glu | Lys | |
| | | | 165 | | | | | 170 | | | | | 175 | | | |
| gca | gga | caa | aaa | tca | agt | ttc | ttc | aaa | gaa | aac | tgt | gtg | aga | aat | aca | 576 |
| Ala | Gly | Gln | Lys | Ser | Ser | Phe | Phe | Lys | Glu | Asn | Cys | Val | Arg | Asn | Thr | |
| | | | 180 | | | | | 185 | | | | | 190 | | | |
| tgt | tat | cta | agg | atg | aac | cga | tat | cca | cct | tgt | ccc | aaa | cca | tcg | gag | 624 |
| Cys | Tyr | Leu | Arg | Met | Asn | Arg | Tyr | Pro | Pro | Cys | Pro | Lys | Pro | Ser | Glu | |
| | | 195 | | | | | 200 | | | | | 205 | | | | |
| gtg | tac | gga | tta | atg | cca | cat | acg | gac | agt | gat | ttc | ctt | aca | atc | ttg | 672 |
| Val | Tyr | Gly | Leu | Met | Pro | His | Thr | Asp | Ser | Asp | Phe | Leu | Thr | Ile | Leu | |
| | 210 | | | | | 215 | | | | | 220 | | | | | |
| tat | caa | gat | caa | gtc | gga | gga | ctc | caa | ctc | atc | aaa | gac | aat | aga | tgg | 720 |
| Tyr | Gln | Asp | Gln | Val | Gly | Gly | Leu | Gln | Leu | Ile | Lys | Asp | Asn | Arg | Trp | |
| 225 | | | | | 230 | | | | | 235 | | | | | 240 | |
| atc | gct | gtt | aaa | cct | aat | cct | aaa | gct | ctc | att | atc | aat | att | ggt | gac | 768 |
| Ile | Ala | Val | Lys | Pro | Asn | Pro | Lys | Ala | Leu | Ile | Ile | Asn | Ile | Gly | Asp | |
| | | | 245 | | | | | 250 | | | | | 255 | | | |
| tta | ttt | cag | gca | tgg | agc | aat | ggc | atg | tac | aaa | agt | gtt | gaa | cac | cgt | 816 |
| Leu | Phe | Gln | Ala | Trp | Ser | Asn | Gly | Met | Tyr | Lys | Ser | Val | Glu | His | Arg | |
| | | | 260 | | | | | 265 | | | | | 270 | | | |

```
gtg atg acg aac cca aag gtg gag aga ttc tca acg gct tat ttt atg     864
Val Met Thr Asn Pro Lys Val Glu Arg Phe Ser Thr Ala Tyr Phe Met
    275                 280                 285 tgt cca tca tac gac gcc gtt ata gag tgt tca agt gat cgt cct gct     912
Cys Pro Ser Tyr Asp Ala Val Ile Glu Cys Ser Ser Asp Arg Pro Ala
290                 295                 300 tat aga aat ttc agc ttc aga gaa ttc aga caa caa gtt caa gaa gat     960
Tyr Arg Asn Phe Ser Phe Arg Glu Phe Arg Gln Gln Val Gln Glu Asp
305                 310                 315                 320 gtt aag aag ttt ggt ttt aaa gtt ggc ctt cct agg ttc ctt aat cac    1008
Val Lys Lys Phe Gly Phe Lys Val Gly Leu Pro Arg Phe Leu Asn His
                325                 330                 335 gtc tac taa                                                        1017
Val Tyr

<210> SEQ ID NO 6
<211> LENGTH: 338
<212> TYPE: PRT
<213> ORGANISM: Arabidopsis

<400> SEQUENCE: 6

Met Asp Pro Pro Phe Asn Glu Ile Tyr Asn Asn Leu Leu Tyr Asn Gln
1               5                   10                  15

Ile Thr Asn Lys Glu Asn Asp Val Ser Glu Ile Pro Phe Ser Phe Ser
            20                  25                  30

Val Thr Ala Val Val Glu Glu Val Glu Leu Pro Val Ile Asp Val Ser
        35                  40                  45

Arg Leu Ile Asp Gly Ala Glu Glu Arg Glu Lys Cys Lys Glu Ala
    50                  55                  60

Ile Ala Arg Ala Ser Arg Glu Trp Gly Phe Phe Gln Val Ile Asn His
65                  70                  75                  80

Gly Ile Ser Met Asp Val Leu Glu Lys Met Arg Gln Glu Gln Ile Arg
                85                  90                  95

Val Phe Arg Glu Pro Phe Asp Lys Lys Ser Lys Ser Glu Lys Phe Ser
            100                 105                 110

Ala Gly Ser Tyr Arg Trp Gly Thr Pro Ser Ala Thr Ser Ile Arg Gln
        115                 120                 125

Leu Ser Trp Ser Glu Ala Phe His Val Pro Met Thr Asp Ile Ser Asp
    130                 135                 140

Asn Lys Asp Phe Thr Thr Leu Ser Ser Thr Met Glu Lys Phe Ala Ser
145                 150                 155                 160

Glu Ser Glu Ala Leu Ala Tyr Met Leu Ala Glu Val Leu Ala Glu Lys
                165                 170                 175

Ala Gly Gln Lys Ser Ser Phe Phe Lys Glu Asn Cys Val Arg Asn Thr
            180                 185                 190

Cys Tyr Leu Arg Met Asn Arg Tyr Pro Pro Cys Pro Lys Pro Ser Glu
        195                 200                 205

Val Tyr Gly Leu Met Pro His Thr Asp Ser Asp Phe Leu Thr Ile Leu
    210                 215                 220

Tyr Gln Asp Gln Val Gly Gly Leu Gln Leu Ile Lys Asp Asn Arg Trp
225                 230                 235                 240

Ile Ala Val Lys Pro Asn Pro Lys Ala Leu Ile Ile Asn Ile Gly Asp
                245                 250                 255

Leu Phe Gln Ala Trp Ser Asn Gly Met Tyr Lys Ser Val Glu His Arg
            260                 265                 270
```

```
Val Met Thr Asn Pro Lys Val Glu Arg Phe Ser Thr Ala Tyr Phe Met
        275                 280                 285

Cys Pro Ser Tyr Asp Ala Val Ile Glu Cys Ser Ser Asp Arg Pro Ala
        290                 295                 300

Tyr Arg Asn Phe Ser Phe Arg Glu Phe Arg Gln Gln Val Gln Glu Asp
305                 310                 315                 320

Val Lys Lys Phe Gly Phe Lys Val Gly Leu Pro Arg Phe Leu Asn His
                325                 330                 335

Val Tyr

<210> SEQ ID NO 7
<211> LENGTH: 378
<212> TYPE: PRT
<213> ORGANISM: Arabidopsis

<400> SEQUENCE: 7

Met Ala Ile Leu Cys Thr Thr Thr Ser Pro Ala Glu Lys Glu His Glu
  1               5                  10                  15

Pro Lys Gln Asp Leu Glu Lys Asp Gln Thr Ser Pro Leu Ile Phe Asn
             20                  25                  30

Pro Ser Leu Leu Asn Leu Gln Ser Gln Ile Pro Asn Gln Phe Ile Trp
         35                  40                  45

Pro Asp Glu Glu Lys Pro Ser Ile Asp Ile Pro Glu Leu Asn Val Pro
     50                  55                  60

Phe Ile Asp Leu Ser Ser Gln Asp Ser Thr Leu Glu Ala Pro Arg Val
 65                  70                  75                  80

Ile Ala Glu Ala Cys Thr Lys His Gly Phe Phe Leu Val Val Asn His
                 85                  90                  95

Gly Val Ser Glu Ser Leu Ile Ala Asp Ala His Arg Leu Met Glu Ser
            100                 105                 110

Phe Phe Asp Met Pro Leu Ala Gly Lys Gln Lys Ala Gln Arg Lys Pro
        115                 120                 125

Gly Glu Ser Cys Gly Tyr Ala Ser Ser Phe Thr Gly Arg Phe Ser Thr
    130                 135                 140

Lys Leu Pro Trp Lys Glu Thr Leu Ser Phe Gln Phe Ser Asn Asp Asn
145                 150                 155                 160

Ser Gly Ser Arg Thr Val Gln Asp Tyr Phe Ser Asp Thr Leu Gly Gln
                165                 170                 175

Glu Phe Glu Gln Phe Gly Lys Val Tyr Gln Asp Tyr Cys Glu Ala Met
            180                 185                 190

Ser Ser Leu Ser Leu Lys Ile Met Glu Leu Leu Gly Leu Ser Leu Gly
        195                 200                 205

Val Asn Arg Asp Tyr Phe Arg Gly Phe Phe Glu Glu Asn Asp Ser Ile
    210                 215                 220

Met Arg Leu Asn His Tyr Pro Pro Cys Gln Thr Pro Asp Leu Thr Leu
225                 230                 235                 240

Gly Thr Gly Pro His Cys Asp Pro Ser Ser Leu Thr Ile Leu His Gln
                245                 250                 255

Asp His Val Asn Gly Leu Gln Val Phe Val Asp Asn Gln Trp Gln Ser
            260                 265                 270

Ile Arg Pro Asn Pro Lys Ala Phe Val Val Asn Ile Gly Asp Thr Phe
        275                 280                 285

Met Ala Leu Ser Asn Gly Ile Phe Lys Ser Cys Leu His Arg Ala Val
    290                 295                 300
```

```
Val Asn Arg Glu Ser Ala Arg Lys Ser Met Ala Phe Phe Leu Cys Pro
305                 310                 315                 320

Lys Lys Asp Lys Val Val Lys Pro Pro Ser Asp Ile Leu Glu Lys Met
            325                 330                 335

Lys Thr Arg Lys Tyr Pro Asp Phe Thr Trp Ser Met Phe Leu Glu Phe
        340                 345                 350

Thr Gln Lys His Tyr Arg Ala Asp Val Asn Thr Leu Asp Ser Phe Ser
    355                 360                 365

Asn Trp Val Ile Thr Asn Asn Asn Pro Ile
370                 375

<210> SEQ ID NO 8
<211> LENGTH: 377
<212> TYPE: PRT
<213> ORGANISM: Arabidopsis

<400> SEQUENCE: 8

Met Ala Val Ser Phe Val Thr Thr Ser Pro Glu Glu Asp Lys Pro
1               5                   10                  15

Lys Leu Gly Leu Gly Asn Ile Gln Thr Pro Leu Ile Phe Asn Pro Ser
            20                  25                  30

Met Leu Asn Leu Gln Ala Asn Ile Pro Asn Gln Phe Ile Trp Pro Asp
        35                  40                  45

Asp Glu Lys Pro Ser Ile Asn Val Leu Glu Leu Asp Val Pro Leu Ile
    50                  55                  60

Asp Leu Gln Asn Leu Leu Ser Asp Pro Ser Ser Thr Leu Asp Ala Ser
65                  70                  75                  80

Arg Leu Ile Ser Glu Ala Cys Lys Lys His Gly Phe Phe Leu Val Val
                85                  90                  95

Asn His Gly Ile Ser Glu Glu Leu Ile Ser Asp Ala His Glu Tyr Thr
            100                 105                 110

Ser Arg Phe Phe Asp Met Pro Leu Ser Glu Lys Gln Arg Val Leu Arg
        115                 120                 125

Lys Ser Gly Glu Ser Val Gly Tyr Ala Ser Ser Phe Thr Gly Arg Phe
    130                 135                 140

Ser Thr Lys Leu Pro Trp Lys Glu Thr Leu Ser Phe Arg Phe Cys Asp
145                 150                 155                 160

Asp Met Ser Arg Ser Lys Ser Val Gln Asp Tyr Phe Cys Asp Ala Leu
                165                 170                 175

Gly His Gly Phe Gln Pro Phe Gly Lys Val Tyr Gln Glu Tyr Cys Glu
            180                 185                 190

Ala Met Ser Ser Leu Ser Leu Lys Ile Met Glu Leu Leu Gly Leu Ser
        195                 200                 205

Leu Gly Val Lys Arg Asp Tyr Phe Arg Glu Phe Phe Glu Glu Asn Asp
    210                 215                 220

Ser Ile Met Arg Leu Asn Tyr Tyr Pro Pro Cys Ile Lys Pro Asp Leu
225                 230                 235                 240

Thr Leu Gly Thr Gly Pro His Cys Asp Pro Thr Ser Leu Thr Ile Leu
                245                 250                 255

His Gln Asp His Val Asn Gly Leu Gln Val Phe Val Glu Asn Gln Trp
            260                 265                 270

Arg Ser Ile Arg Pro Asn Pro Lys Ala Phe Val Val Asn Ile Gly Asp
        275                 280                 285

Thr Phe Met Ala Leu Ser Asn Asp Arg Tyr Lys Ser Cys Leu His Arg
    290                 295                 300
```

```
Ala Val Val Asn Ser Glu Arg Met Arg Lys Ser Leu Ala Phe Phe Leu
305                 310                 315                 320

Cys Pro Lys Lys Asp Arg Val Val Thr Pro Pro Arg Glu Leu Leu Asp
                325                 330                 335

Ser Ile Thr Ser Arg Arg Tyr Pro Asp Phe Thr Trp Ser Met Phe Leu
                340                 345                 350

Glu Phe Thr Gln Lys His Tyr Arg Ala Asp Met Asn Thr Leu Gln Ala
            355                 360                 365

Phe Ser Asp Trp Leu Thr Lys Pro Ile
            370                 375

<210> SEQ ID NO 9
<211> LENGTH: 358
<212> TYPE: PRT
<213> ORGANISM: Arabidopsis

<400> SEQUENCE: 9

Met Pro Ala Met Leu Thr Asp Val Phe Arg Gly His Pro Ile His Leu
 1               5                  10                  15

Pro His Ser His Ile Pro Asp Phe Thr Ser Leu Arg Glu Leu Pro Asp
                20                  25                  30

Ser Tyr Lys Trp Thr Pro Lys Asp Leu Leu Phe Ser Ala Ala Pro
            35                  40                  45

Ser Pro Pro Ala Thr Gly Glu Asn Ile Pro Leu Ile Asp Leu Asp His
    50                  55                  60

Pro Asp Ala Thr Asn Gln Ile Gly His Ala Cys Arg Thr Trp Gly Ala
65                  70                  75                  80

Phe Gln Ile Ser Asn His Gly Val Pro Leu Gly Leu Leu Gln Asp Ile
                85                  90                  95

Glu Phe Leu Thr Gly Ser Leu Phe Gly Leu Pro Val Gln Arg Lys Leu
            100                 105                 110

Lys Ser Ala Arg Ser Glu Thr Gly Val Ser Gly Tyr Gly Val Ala Arg
        115                 120                 125

Ile Ala Ser Phe Phe Asn Lys Gln Met Trp Ser Glu Gly Phe Thr Ile
    130                 135                 140

Thr Gly Ser Pro Leu Asn Asp Phe Arg Lys Leu Trp Pro Gln His His
145                 150                 155                 160

Leu Asn Tyr Cys Asp Ile Val Glu Glu Tyr Glu His Met Lys Lys
                165                 170                 175

Leu Ala Ser Lys Leu Met Trp Leu Ala Leu Asn Ser Leu Gly Val Ser
            180                 185                 190

Glu Glu Asp Ile Glu Trp Ala Ser Leu Ser Ser Asp Leu Asn Trp Ala
        195                 200                 205

Gln Ala Ala Leu Gln Leu Asn His Tyr Pro Val Cys Pro Glu Pro Asp
    210                 215                 220

Arg Ala Met Gly Leu Ala Ala His Thr Asp Ser Thr Leu Leu Thr Ile
225                 230                 235                 240

Leu Tyr Gln Asn Asn Thr Ala Gly Leu Gln Val Phe Arg Asp Asp Leu
                245                 250                 255

Gly Trp Val Thr Val Pro Pro Phe Pro Gly Ser Leu Val Val Asn Val
            260                 265                 270

Gly Asp Leu Phe His Ile Leu Ser Asn Gly Leu Phe Lys Ser Val Leu
        275                 280                 285

His Arg Ala Arg Val Asn Gln Thr Arg Ala Arg Leu Ser Val Ala Phe
```

```
               290                 295                 300
Leu Trp Gly Pro Gln Ser Asp Ile Lys Ile Ser Pro Val Pro Lys Leu
305                 310                 315                 320

Val Ser Pro Val Glu Ser Pro Leu Tyr Gln Ser Val Thr Trp Lys Glu
                325                 330                 335

Tyr Leu Arg Thr Lys Ala Thr His Phe Asn Lys Ala Leu Ser Met Ile
                340                 345                 350

Arg Asn His Arg Glu Glu
        355

<210> SEQ ID NO 10
<211> LENGTH: 330
<212> TYPE: PRT
<213> ORGANISM: Arabidopsis

<400> SEQUENCE: 10

Met Ala Val Leu Ser Lys Pro Val Ala Ile Pro Lys Ser Gly Phe Ser
  1               5                  10                  15

Leu Ile Pro Val Ile Asp Met Ser Asp Pro Glu Ser Lys His Ala Leu
                 20                  25                  30

Val Lys Ala Cys Glu Asp Phe Gly Phe Phe Lys Val Ile Asn His Gly
             35                  40                  45

Val Ser Ala Glu Leu Val Ser Val Leu Glu His Glu Thr Val Asp Phe
         50                  55                  60

Phe Ser Leu Pro Lys Ser Glu Lys Thr Gln Val Ala Gly Tyr Pro Phe
 65                  70                  75                  80

Gly Tyr Gly Asn Ser Lys Ile Gly Arg Asn Gly Asp Val Gly Trp Val
                 85                  90                  95

Glu Tyr Leu Leu Met Asn Ala Asn His Asp Ser Gly Ser Gly Gly Pro
                100                 105                 110

Leu Phe Pro Ser Leu Leu Lys Ser Pro Gly Thr Phe Arg Asn Ala Leu
            115                 120                 125

Glu Glu Tyr Thr Thr Ser Val Arg Lys Met Thr Phe Asp Val Leu Glu
        130                 135                 140

Lys Ile Thr Asp Gly Leu Gly Ile Lys Pro Arg Asn Thr Leu Ser Lys
145                 150                 155                 160

Leu Val Ser Asp Gln Asn Thr Asp Ser Ile Leu Arg Leu Asn His Tyr
                165                 170                 175

Pro Pro Cys Pro Leu Ser Asn Lys Lys Thr Asn Gly Gly Lys Asn Val
            180                 185                 190

Ile Gly Phe Gly Glu His Thr Asp Pro Gln Ile Ile Ser Val Leu Arg
        195                 200                 205

Ser Asn Asn Thr Ser Gly Leu Gln Ile Asn Leu Asn Asp Gly Ser Trp
    210                 215                 220

Ile Ser Val Pro Pro Asp His Thr Ser Phe Phe Asn Val Gly Asp
225                 230                 235                 240

Ser Leu Gln Val Met Thr Asn Gly Arg Phe Lys Ser Val Arg His Arg
                245                 250                 255

Val Leu Ala Asn Cys Lys Lys Ser Arg Val Ser Met Ile Tyr Phe Ala
            260                 265                 270

Gly Pro Ser Leu Thr Gln Arg Ile Ala Pro Leu Thr Cys Leu Ile Asp
        275                 280                 285

Asn Glu Asp Glu Arg Leu Tyr Glu Glu Phe Thr Trp Ser Glu Tyr Lys
    290                 295                 300
```

```
Asn Ser Thr Tyr Asn Ser Arg Leu Ser Asp Asn Arg Leu Gln Gln Phe
305                 310                 315                 320

Glu Arg Lys Thr Ile Lys Asn Leu Leu Asn
                325                 330

<210> SEQ ID NO 11
<211> LENGTH: 342
<212> TYPE: PRT
<213> ORGANISM: Arabidopsis

<400> SEQUENCE: 11

Met Val Val Leu Pro Gln Pro Val Thr Leu Asp Asn His Ile Ser Leu
 1               5                  10                  15

Ile Pro Thr Tyr Lys Pro Val Pro Val Leu Thr Ser His Ser Ile Pro
                20                  25                  30

Val Val Asn Leu Ala Asp Pro Glu Ala Lys Thr Arg Ile Val Lys Ala
                35                  40                  45

Cys Glu Glu Phe Gly Phe Phe Lys Val Val Asn His Gly Val Arg Pro
 50                  55                  60

Glu Leu Met Thr Arg Leu Glu Gln Ala Ile Gly Phe Phe Gly Leu
 65                  70                  75                  80

Pro Gln Ser Leu Lys Asn Arg Ala Gly Pro Pro Glu Pro Tyr Gly Tyr
                 85                  90                  95

Gly Asn Lys Arg Ile Gly Pro Asn Gly Asp Val Gly Trp Ile Glu Tyr
                100                 105                 110

Leu Leu Leu Asn Ala Asn Pro Gln Leu Ser Ser Pro Lys Thr Ser Ala
                115                 120                 125

Val Phe Arg Gln Thr Pro Gln Ile Phe Arg Asn Ala Leu Glu Glu Tyr
130                 135                 140

Thr Thr Ser Val Arg Lys Met Thr Phe Asp Val Leu Glu Lys Ile Thr
145                 150                 155                 160

Asp Gly Leu Gly Ile Lys Pro Arg Asn Thr Leu Ser Lys Leu Val Ser
                165                 170                 175

Asp Gln Asn Thr Asp Ser Ile Leu Arg Leu Asn His Tyr Pro Pro Cys
                180                 185                 190

Pro Leu Ser Asn Lys Lys Thr Asn Gly Gly Lys Asn Val Ile Gly Phe
                195                 200                 205

Gly Glu His Thr Asp Pro Gln Ile Ile Ser Val Leu Arg Ser Asn Asn
210                 215                 220

Thr Ser Gly Leu Gln Ile Asn Leu Asn Asp Gly Ser Trp Ile Ser Val
225                 230                 235                 240

Pro Pro Asp His Thr Ser Phe Phe Asn Val Gly Asp Ser Leu Gln
                245                 250                 255

Val Met Thr Asn Gly Arg Phe Lys Ser Val Arg His Arg Val Leu Ala
                260                 265                 270

Asn Cys Lys Lys Ser Arg Val Ser Met Ile Tyr Phe Ala Gly Pro Ser
                275                 280                 285

Leu Thr Gln Arg Ile Ala Pro Leu Cys Leu Ile Asp Asn Glu Asp Glu
                290                 295                 300

Arg Leu Tyr Glu Glu Phe Thr Trp Ser Glu Tyr Lys Asn Ser Thr Tyr
305                 310                 315                 320

Asn Ser Arg Leu Ser Asp Asn Arg Leu Gln Gln Phe Glu Arg Lys Thr
                325                 330                 335

Ile Lys Asn Leu Leu Asn
                340
```

```
<210> SEQ ID NO 12
<211> LENGTH: 335
<212> TYPE: PRT
<213> ORGANISM: Arabidopsis

<400> SEQUENCE: 12

Met Val Ile Val Leu Gln Pro Ala Ser Phe Asp Ser Asn Leu Tyr Val
  1               5                  10                  15

Asn Pro Lys Cys Lys Pro Arg Pro Val Leu Ile Pro Val Ile Asp Leu
             20                  25                  30

Thr Asp Ser Asp Ala Lys Thr Gln Ile Val Lys Ala Cys Glu Glu Phe
         35                  40                  45

Gly Phe Phe Lys Val Ile Asn His Gly Val Arg Pro Asp Leu Leu Thr
     50                  55                  60

Gln Leu Glu Gln Glu Ala Ile Asn Phe Phe Ala Leu His His Ser Leu
 65                  70                  75                  80

Lys Asp Lys Ala Gly Pro Pro Asp Pro Phe Gly Tyr Gly Thr Lys Arg
                 85                  90                  95

Ile Gly Pro Asn Gly Asp Leu Gly Trp Leu Glu Tyr Ile Leu Leu Asn
            100                 105                 110

Ala Asn Leu Cys Leu Glu Ser His Lys Thr Thr Ala Ile Phe Arg His
        115                 120                 125

Thr Pro Ala Ile Phe Arg Glu Ala Val Glu Glu Tyr Ile Lys Glu Met
    130                 135                 140

Lys Arg Met Ser Ser Lys Phe Leu Glu Met Val Glu Glu Glu Leu Lys
145                 150                 155                 160

Ile Glu Pro Lys Glu Lys Leu Ser Arg Leu Val Lys Val Lys Glu Ser
                165                 170                 175

Asp Ser Cys Leu Arg Met Asn His Tyr Pro Glu Lys Glu Glu Thr Pro
            180                 185                 190

Val Lys Glu Glu Ile Gly Phe Gly Glu His Thr Asp Pro Gln Leu Ile
        195                 200                 205

Ser Leu Leu Arg Ser Asn Asp Thr Glu Gly Leu Gln Ile Cys Val Lys
    210                 215                 220

Asp Gly Thr Trp Val Asp Val Thr Pro Asp His Ser Ser Phe Phe Val
225                 230                 235                 240

Leu Val Gly Asp Thr Leu Gln Val Met Thr Asn Gly Arg Phe Lys Ser
                245                 250                 255

Val Lys His Arg Val Val Thr Asn Thr Lys Arg Ser Arg Ile Ser Met
            260                 265                 270

Ile Tyr Phe Ala Gly Pro Pro Leu Ser Glu Lys Ile Ala Pro Leu Ser
        275                 280                 285

Cys Leu Val Pro Lys Gln Asp Asp Cys Leu Tyr Asn Glu Phe Thr Trp
    290                 295                 300

Ser Gln Tyr Lys Leu Ser Ala Tyr Lys Thr Lys Leu Gly Asp Tyr Arg
305                 310                 315                 320

Leu Gly Leu Phe Glu Lys Arg Pro Pro Phe Ser Leu Ser Asn Val
                325                 330                 335
```